United States Patent
Yu et al.

(10) Patent No.: US 10,927,177 B2
(45) Date of Patent: Feb. 23, 2021

(54) METHODS OF TREATMENT USING ANTI-C-MET ANTIBODIES

(71) Applicant: VIROMED CO., LTD., Seoul (KR)

(72) Inventors: Seung Shin Yu, Seoul (KR); Jae-Gyun Jeong, Seoul (KR); Dongsik Kim, Seoul (KR); Juwon Shim, Anyang-si (KR)

(73) Assignee: Helixmith Co., Ltd, Seoul (KR)

( * ) Notice: Subject to any disclaimer, the term of this patent is extended or adjusted under 35 U.S.C. 154(b) by 145 days.

(21) Appl. No.: 16/075,304

(22) PCT Filed: Feb. 6, 2017

(86) PCT No.: PCT/KR2017/001296
§ 371 (c)(1),
(2) Date: Aug. 3, 2018

(87) PCT Pub. No.: WO2017/135791
PCT Pub. Date: Aug. 10, 2017

(65) Prior Publication Data
US 2019/0315872 A1   Oct. 17, 2019

Related U.S. Application Data

(60) Provisional application No. 62/291,988, filed on Feb. 5, 2016.

(51) Int. Cl.
| | | |
|---|---|---|
| *A61K 39/395* | (2006.01) | |
| *A61P 13/12* | (2006.01) | |
| *A61P 9/10* | (2006.01) | |
| *A61P 25/28* | (2006.01) | |
| *A61P 17/02* | (2006.01) | |
| *C07K 16/28* | (2006.01) | |
| *C07K 14/47* | (2006.01) | |
| *C07K 14/475* | (2006.01) | |
| *A61K 39/00* | (2006.01) | |

(52) U.S. Cl.
CPC ........ *C07K 16/2863* (2013.01); *A61K 39/395* (2013.01); *A61K 39/3955* (2013.01); *A61K 39/39558* (2013.01); *A61P 9/10* (2018.01); *A61P 13/12* (2018.01); *A61P 17/02* (2018.01); *A61P 25/28* (2018.01); *A61K 2039/505* (2013.01); *A61K 2039/54* (2013.01); *C07K 14/4753* (2013.01); *C07K 2317/24* (2013.01); *C07K 2317/622* (2013.01); *C07K 2317/75* (2013.01)

(58) Field of Classification Search
CPC ................... A61K 39/3955; C07K 16/2863
See application file for complete search history.

(56) References Cited

U.S. PATENT DOCUMENTS

| | | |
|---|---|---|
| 8,398,974 B2 | 3/2013 | Davies et al. |
| 8,765,128 B2 | 7/2014 | Goetsch et al. |
| 2013/0129731 A1 | 5/2013 | Kim et al. |
| 2014/0193431 A1 | 7/2014 | Park et al. |
| 2017/0233492 A1 | 8/2017 | Yoo et al. |

FOREIGN PATENT DOCUMENTS

| | | |
|---|---|---|
| EP | 2287197 A1 | 2/2011 |
| KR | 10-2016-0017918 A | 2/2016 |
| WO | WO-2016/021864 A1 | 2/2016 |

OTHER PUBLICATIONS

Mizuno et al, 2008. Frontiers in Bioscience. 13: 7072-7086.*
Kim et al (2019. Scientific Reports. 9: 13495; pp. 1-12 as printed).*
Extended European Search Report dated Mar. 15, 2019 for European Patent Application No. 17747834.4, Yu et al., "Anti-C-Met Antibodies and Uses Thereof," filed Feb. 6, 2017 (9 pages).
Gallo et al., "Agonist antibodies activating the Met receptor protect cardiomyoblasts from cobalt chloride-induced apoptosis and autophagy," Cell Death Dis. 5:e1185 (2014) (12 pages).
Prat et al., "Monoclonal antibodies against the MET/HGF receptor and its ligand: multitask tools with applications from basic research to therapy," Biomedicines. 2(4):359-83 (2014).
International Search Report dated Jun. 12, 2017 for International Patent Application No. PCT/KR2017/001296, Yu et al., "Anti-C-Met Antibodies and Uses Thereof," filed Feb. 6, 2017 (7 pages).
Prat et al., "Agonistic monoclonal antibodies against the Met receptor dissect the biological responses to HGF," J Cell Sci. 111(Pt 2):237-247 (1998).

* cited by examiner

*Primary Examiner* — Zachary C Howard
(74) *Attorney, Agent, or Firm* — Clark & Elbing LLP; Susan M. Michaud

(57) ABSTRACT

The present disclosure provides a pharmaceutical composition for preventing or treating a variety of diseases through c-Met activation in cells induced by the anti-c-Met antibody described herein which functions as a c-Met agonist. The current invention concerns a method for preventing or treating various diseases through c-Met activation by the anti-c-Met antibody described herein.

18 Claims, 16 Drawing Sheets
Specification includes a Sequence Listing.

* A significant difference at p<0.05 level compared to the PBS

Naive

PBS

1E4 10 mg/kg

1. Score 1: Injured area is below 10% in whole
2. Score 2: Injured area is between 10%-40% in whole kidney tissue
3. Score 3: Injured area is between 40%-70% in whole kidney tissue
4. Score 4: Injured area is more than 70% in whole kidney tissue

* A significant difference at $p<0.05$ level compared to the PBS

Control

PBS

1E4

*//* A significant difference at $p<0.001/p<0.01/p<0.05$ level compared to the PBS

**/* A significant difference at p<0.01/p<0.05 level compared to the PBS

METHODS OF TREATMENT USING ANTI-C-MET ANTIBODIES

CROSS-REFERENCE TO RELATED APPLICATIONS

This application claims priority to and the benefit of U.S. Patent Application No. 62/291,988 filed in the United States Patent and Trademark Office on 5 Feb. 2016, the entire contents of which are incorporated herein by reference.

TECHNICAL FIELD

The subject matter described herein relates to methods for treating subjects with an antibody which specifically binds the c-MET protein wherein the binding activates c-Met activities such as phosphorylation of c-Met and/or activation of MDCK-2 scattering. The anti-c-Met antibodies are useful in the prevention or treatment of a variety of diseases or disorders.

BACKGROUND

Expressed on the cell surface, c-Met (mesenchymal-epithelial transition factor) is a receptor tyrosine kinase that is encoded by the Met proto-oncogene. Structurally, c-Met is a disulfide-linked heterodimer composed of an extracellular alpha subunit (50 kDa) and a transmembrane beta subunit (140 kDa), which can be characterized with an extracellular domain for ligand binding, a membrane-spanning segment, and a tyrosine kinase catalytic motif involved in phosphorylation of tyrosine residues within this intracellular domain. (Dean et al., Nature, 4: 318 (6044): 385, 1985; Park et al., PNAS, 84 (18): 6379, 1976; Maggiora et al., J. Cell Physiol., 173:183, 1997).

Upon binding to its ligand HGF (hepatocyte growth factor), c-Met dimerizes and autophosphorylates on cytoplasmic tyrosine residues, then in turn interacts with various proteins that mediate downstream signaling pathways. c-Met activation results in a variety of biological responses which lead to increased cell growth, scattering and motility, invasion, protection from apoptosis, branching morphogenesis, and angiogenesis. Under pathological conditions, improper activation of c-Met may confer proliferative, survival and invasive/metastatic abilities of cancer cells. Given the variety of biological and physiological functions impacted by c-Met activity, the c-Met protein has become a versatile therapeutic target. Provided herein are a c-Met immunoglobulins which bind to and activate the c-Met protein and which are prophylactically and/or therapeutically effective in a variety of disorders or diseases.

The foregoing examples of the related art and limitations related therewith are intended to be illustrative and not exclusive. Other limitations of the related art will become apparent to those of skill in the art upon a reading of the specification and a study of the drawings.

BRIEF SUMMARY

The following aspects and embodiments thereof described and illustrated below are meant to be exemplary and illustrative, not limiting in scope.

In one aspect, a method for treating a subject in need thereof is provided, comprising administering to the subject a therapeutically effective amount of a polypeptide or a pharmaceutical composition comprising the polypeptide, wherein the polypeptide comprises an immunoglobulin heavy chain variable domain which comprises a CDR1 of SEQ ID NO:5, a CDR2 of SEQ ID NO:6, and a CDR3 of SEQ ID NO:7 and a light chain variable domain which comprises a CDR1 of SEQ ID NO:8, a CDR2 of SEQ ID NO:9 and a CDR3 of SEQ ID NO:10.

In one aspect, a method for treating a subject at risk of stroke or who has experienced a stroke is provided, comprising administering to the subject a therapeutically effective amount of a polypeptide or a pharmaceutical composition comprising the polypeptide, wherein the polypeptide comprises an immunoglobulin heavy chain variable domain which comprises a CDR1 of SEQ ID NO:5, a CDR2 of SEQ ID NO:6, and a CDR3 of SEQ ID NO:7 and a light chain variable domain which comprises a CDR1 of SEQ ID NO:8, a CDR2 of SEQ ID NO:9 and a CDR3 of SEQ ID NO:10.

In one aspect, a method for treating a subject at risk of a kidney injury or disease or who has been diagnosed with a kidney injury or disease is provided, comprising administering to the subject a therapeutically effective amount of a polypeptide or a pharmaceutical composition comprising the polypeptide, wherein the polypeptide comprises an immunoglobulin heavy chain variable domain which comprises a CDR1 of SEQ ID NO:5, a CDR2 of SEQ ID NO:6, and a CDR3 of SEQ ID NO:7 and a light chain variable domain which comprises a CDR1 of SEQ ID NO:8, a CDR2 of SEQ ID NO:9 and a CDR3 of SEQ ID NO:10.

In some embodiments, the kidney injury or disease is a fibrotic condition.

In some embodiments, the kidney injury or disease is selected from the group consisting of renal fibrosis, chronic kidney fibrosis, chronic nephropathy associated with diabetes, lupus, scleroderma of the kidney, glomerular nephritis, focal segmental glomerular sclerosis, IgA nephropathyrenal fibrosis associated with human chronic kidney disease (CKD), chronic progressive nephropathy (CPN), tubulointerstitial fibrosis, ureteral obstruction, chronic uremia, chronic interstitial nephritis, radiation nephropathy, glomerulosclerosis, progressive glomerulonephrosis (PGN), endothelial/thrombotic microangiopathy injury, HIV-associated nephropathy, and a fibrosis associated with exposure to a toxin, an irritant, or a chemotherapeutic agent.

In one aspect, a method for promoting wound healing in a subject in need thereof is provided, comprising administering to the subject a therapeutically effective amount of a polypeptide or a pharmaceutical composition comprising the polypeptide, wherein the polypeptide comprises an immunoglobulin heavy chain variable domain which comprises a CDR1 of SEQ ID NO:5, a CDR2 of SEQ ID NO:6, and a CDR3 of SEQ ID NO:7 and a light chain variable domain which comprises a CDR1 of SEQ ID NO:8, a CDR2 of SEQ ID NO:9 and a CDR3 of SEQ ID NO:10.

In some embodiments, the wound is a mechanical, chemical, bacterial, or thermal wound.

In some embodiments, the wound is selected from the group consisting of an incision, a laceration, an abrasion, a puncture wound, a penetration wound, and a gunshot wound.

In some embodiments, the wound is a skin wound.

In one aspect, a method for treating a subject at risk of a retinal neovascularization disorder or who has been diagnosed with a retinal neovascularization disorder is provided, comprising administering to the subject a therapeutically effective amount of a polypeptide or a pharmaceutical composition comprising the polypeptide, wherein the polypeptide comprises an immunoglobulin heavy chain variable domain which comprises a CDR1 of SEQ ID NO:5, a CDR2 of SEQ ID NO:6, and a CDR3 of SEQ ID NO:7 and a light chain variable domain which comprises a CDR1 of SEQ ID NO:8, a CDR2 of SEQ ID NO:9 and a CDR3 of SEQ ID NO:10.

In some embodiments, the retinal neovascularization disorder is caused by a member selected from the group consisting of macular degeneration, histoplasmosis, pathological myopia, angioid streaks, anterior ischemic optic neuropathy, bacterial endocarditis, Best's disease, birdshot retinochoroidopathy, choroidal hemangioma, choroidal nevi, choroidal nonperfusion, choroidal osteomas, choroidal rupture, choroideremia, chronic retinal detachment, coloboma of the retina, Drusen, endogenous *Candida endophthalmitis*, extrapapillary hamartomas of the retinal pigmented epithelium, fundus flavimaculatus, idiopathic, macular hole, malignant melanoma, membranoproliferative glomerulonephritis (type II), metallic intraocular foreign body, morning glory disc syndrome, multiple evanescent white-dot syndrome (MEWDS), neovascularization at ora *Serrata*, operating microscope burn, optic nerve head pits, photocoagulation, punctuate inner choroidopathy, rubella, sarcoidosis, serpiginous or geographic choroiditis, subretinal fluid drainage, tilted disc syndrome, Taxoplasma retinochoroiditis, tuberculosis, Vogt-Koyanagi-Harada syndrome, diabetic retinopathy, non-diabetic retinopathy, branch vein occlusion, central retinal vein occlusion, retinopathy in premature infants, rubeosis iridis, neovascular glaucoma, periofoveal telangiectasis, sickle cell retinopathy, Eale's disease, retinal vasculitis, Von Hippel Linau disease, radiation retinopathy, retinal cryoinjury, retinitis pigmentosa, retinochoroidal coloboma, corneal neovascularization due to herpes simplex keratitis, corneal ulcers, keratoplasty, pterigyia, and trauma.

In some embodiments, the retinal neovascularization disorder is choroidal neovascularization.

In one aspect, a method for treating a subject who has been diagnosed with a neurological disorder or disease is provided, comprising administering to the subject a therapeutically effective amount of a polypeptide or a pharmaceutical composition comprising the polypeptide, wherein the polypeptide comprises an immunoglobulin heavy chain variable domain which comprises a CDR1 of SEQ ID NO:5, a CDR2 of SEQ ID NO:6, and a CDR3 of SEQ ID NO:7 and a light chain variable domain which comprises a CDR1 of SEQ ID NO:8, a CDR2 of SEQ ID NO:9 and a CDR3 of SEQ ID NO:10.

In some embodiments, the neurological disorder or disease is selected from the group consisting of traumatic brain injury, stroke, cerebral aneurism, spinal cord injury, Parkinson's disease, amyotrophic lateral sclerosis, Alzheimer's disease, diffuse cerebral cortical atrophy, Lewy-body dementia, Pick disease, mesolimbocortical dementia, thalamic degeneration, Huntington chorea, cortical-striatal-spinal degeneration, cortical-basal ganglionic degeneration, cerebrocerebellar degeneration, familial dementia with spastic paraparesis, polyglucosan body disease, Shy-Drager syndrome, olivopontocerebellar atrophy, progressive supranuclear palsy, dystonia musculorum deformans, Hallervorden-Spatz disease, Meige syndrome, familial tremors, Gilles de la Tourette syndrome, acanthocytic chorea, Friedreich ataxia, Holmes familial cortical cerebellar atrophy, Gerstmann-Straussler-Scheinker disease, progressive spinal muscular atrophy, progressive balbar palsy, primary lateral sclerosis, hereditary muscular atrophy, spastic paraplegia, peroneal muscular atrophy, hypertrophic interstitial polyneuropathy, heredopathia atactica polyneuritiformis, optic neuropathy, ophthalmoplegia, and retina or optic nerve damage.

In one aspect, a method for administering to the subject the polypeptide is provided, wherein the polypeptide comprises the immunoglobulin heavy chain variable domain which comprises a CDR1 of SEQ ID NO:5, a CDR2 of SEQ ID NO:6, and a CDR3 of SEQ ID NO:7 and the light chain variable domain which comprises a CDR1 of SEQ ID NO:8, a CDR2 of SEQ ID NO:9 and a CDR3 of SEQ ID NO:10.

In some embodiments, the method of administering is intravenous, parenteral, intravitreal, intrathecal, subcutaneous, topical, transdermal or by infusion.

In some embodiments, the subject is not suffering from a cancer. In other embodiments, the subject has not been diagnosed with a cancer.

In some embodiments, the polypeptide is an antibody or fragment thereof.

In some embodiments, the heavy chain variable domain comprises SEQ ID NO:1 and the light chain variable domain comprises SEQ ID NO:2.

In some embodiments, the antibody or fragment thereof is a human, chimeric or humanized antibody or fragment thereof.

In some embodiments, the polypeptide comprises a ScFv. In other embodiments, the scFv heavy chain variable domain comprises SEQ ID NO:1 and the light chain variable domain comprises SEQ ID NO:2. In still other embodiments, the scFv comprises SEQ ID NO:3.

In one aspect, a pharmaceutical composition for treating an ischemic disorder, a stroke, a kidney injury or disease, a retinal neovascularization disorder, a neurological disorder or disease, or a wound, comprising an antibody or fragment thereof which binds to c-Met (mesenchymal-epithelial transition factor) as an active ingredient and a pharmaceutically acceptable carrier is provided, wherein the antibody comprises: an heavy chain variable domain which comprises a CDR1 of SEQ ID NO:5, a CDR2 of SEQ ID NO:6, and a CDR3 of SEQ ID NO:7; and an light chain variable domain which comprises a CDR1 of SEQ ID NO:8, a CDR2 of SEQ ID NO:9 and a CDR3 of SEQ ID NO:10.

In some embodiments, the heavy chain variable domain comprises SEQ ID NO:1 and the light chain variable domain comprises SEQ ID NO:2.

In one aspect, a pharmaceutical composition for treating an ischemic disorder, a stroke, a kidney injury or disease, a retinal neovascularization disorder, a neurological disorder or disease, or a wound, comprising a scFv which binds to c-Met as an active ingredient and a pharmaceutically acceptable carrier is provided, wherein the scFv comprises: an heavy chain variable domain comprises SEQ ID NO:1 and the light chain variable domain comprises SEQ ID NO:2.

In some embodiments, the scFv comprises SEQ ID NO:3.

Additional embodiments of the present methods and compositions, and the like, will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims, particularly when considered in conjunction with the accompanying examples and drawings.

BRIEF DESCRIPTION OF DRAWINGS

FIG. 1A is a photograph of a epidermal lesion on Day 10 after the wound occurred in mice. FIG. 1B is a graph illustrating the kinetics of wound closure for 14 days in mice treated with the agonist anti-c-Met antibody.

FIG. 2A is a graph showing the change in the levels of blood urea nitrogen (BUN) and FIG. 2B is a graph showing the change in the levels of blood creatinine (Crea) in mice with renal injury which were treated with agonist anti-c-Met antibody-treated mice with renal injury. Naïve refers to animals treated with neither ADR nor antibody. PBS refers to animals treated with ADR then with phosphate buffered saline (no antibody).

FIG. 4A shows representative images of Masson's trichrome-stained sections of injured kidney tissues induced by UUO. FIG. 4B is a corresponding graph illustrating the score of fibrosis measured in the images of FIG. 4A.

FIG. 7A shows images of stained cells. FIG. 7B is a quantitative representation of the images shown in FIG. 7A.

BRIEF DESCRIPTION OF THE SEQUENCES

Figure 1A:
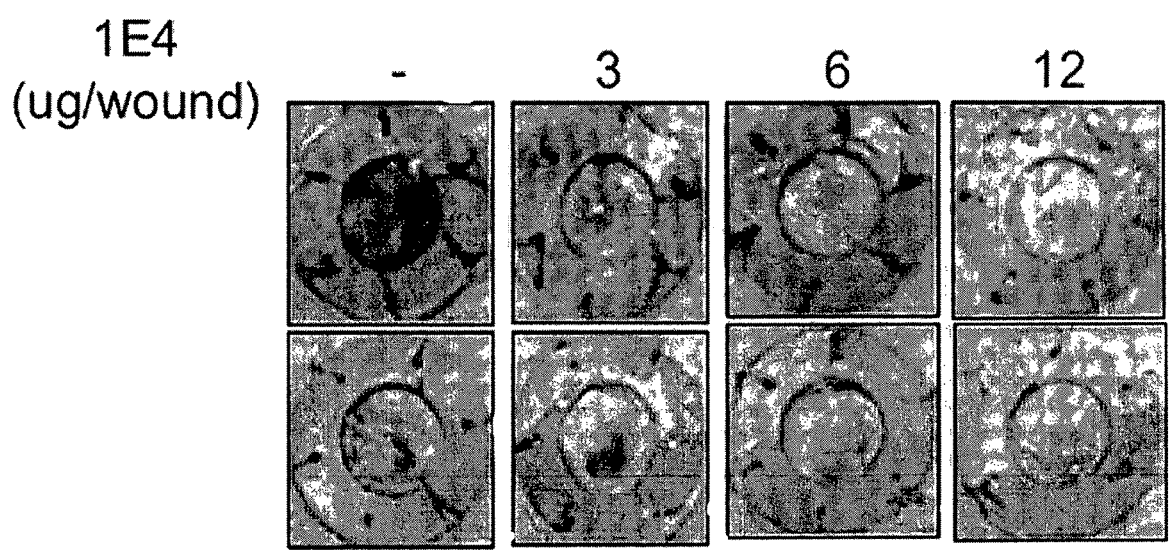
FIGS. 1A-1B show a wound-healing promoting effect of an agonist anti-c-Met antibody.

SEQ ID NO:1 is the amino acid sequence of the 1E4 heavy chain variable domain.

SEQ ID NO:2 is the amino acid sequence of the 1E4 light chain variable domain.

SEQ ID NO:3 is the amino acid sequence of the 1E4 scFv construct.

SEQ ID NO:4 is the amino acid sequence of the linker domain in the 1E4 scFv construct.

SEQ ID NO:5 is the amino acid sequence of the 1E4 heavy chain variable domain CDR1.

SEQ ID NO:6 is the amino acid sequence of the 1E4 heavy chain variable domain CDR2.

SEQ ID NO:7 is the amino acid sequence of the 1E4 heavy chain variable domain CDR3.

SEQ ID NO:8 is the amino acid sequence of the 1E4 light chain variable domain CDR1.

SEQ ID NO:9 is the amino acid sequence of the 1E4 light chain variable domain CDR2.

SEQ ID NO:10 is the amino acid sequence of the 1E4 light chain variable domain CDR3.

SEQ ID NO:11 is the nucleic acid sequence of the 1E4 heavy chain variable domain.

SEQ ID NO:12 is the nucleic acid sequence of the 1E4 light chain variable domain.

SEQ ID NO:13 is the amino acid sequence of a human c-Met protein isoform b as described in GenBank Acc. No. NP_000236).

SEQ ID NO:14 is the amino acid sequence of human c-Met protein isoform a as described in GenBank Acc. No. NP_001120972).

SEQ ID NO:15 is the amino acid sequence of a mouse c-Met protein as described in GenBank Acc. No. NP_032617).

DETAILED DESCRIPTION

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

I. DEFINITIONS

As used in this specification, the singular forms "a," "an," and "the" include plural referents unless the context clearly dictates otherwise. Thus, for example, reference to a "polymer" includes a single polymer as well as two or more of the same or different polymers, reference to an "excipient" includes a single excipient as well as two or more of the same or different excipients, and the like.

Where a range of values is provided, it is intended that each intervening value between the upper and lower limit of that range and any other stated or intervening value in that stated range is encompassed within the disclosure. For example, if a range of 1 μm to 8 μm is stated, it is intended that 2 μm, 3 μm, 4 μm, 5 μm, 6 μm, and 7 μm are also explicitly disclosed, as well as the range of values greater than or equal to 1 μm and the range of values less than or equal to 8 μm.

The term "c-Met" herein refers to the MET proto-oncogene, receptor tyrosine kinase protein product which is also known in the art as the hepatocyte growth factor receptor (HGFR). Examples of c-Met include but are not limited to protein products described in GenBank as Accession No. NP_00236 (human c-Met isoform b, SEQ ID NO:13), NP_001120972 (human c-Met isoform a, SEQ ID NO:14) and NP_032617 (mouse, SEQ ID NO:15) and variants thereof which are bound by the 1E4 polypeptides described herein.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

The term "chimeric" antibody refers to an antibody in which a portion of the heavy and/or light chain is derived from a particular source or species, while the remainder of the heavy and/or light chain is derived from a different source or species.

The terms "full length antibody," "intact antibody," and "whole antibody" are used herein interchangeably to refer to an antibody having a structure substantially similar to a native antibody structure or having heavy chains that contain an Fc region as defined herein.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG$_3$, IgG$_4$, IgA$_1$, and IgA$_2$. The heavy chain constant domains that correspond to the different classes of immunoglobulins are called α, δ, ε, γ, and μ, respectively.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen.

The "Fab" fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3 (L3)-FR4.

"Fv" is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three HVRs of each variable domain interact to define an antigen-binding site on the surface of the VH-VL dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. Kuby Immunology, 6th ed., W.H. Freeman and Co., page 91 (2007)). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., J. Immunol. 150:880-887 (1993); Clarkson et al., Nature 352:624-628 (1991).

The term "specifically binds," or the like, means that an antibody or antigen-binding fragment thereof, or other construct such as an scFv, forms a complex with an antigen that is relatively stable under physiologic conditions. Specific binding can be characterized by an equilibrium dissociation constant of at least about $1 \times 10^{-6}$ M or less (e.g., a smaller $K_D$ denotes a tighter binding). Methods for determining whether two molecules specifically bind are well known in the art and include, for example, equilibrium dialysis, surface plasmon resonance, and the like. An isolated antibody that specifically binds human c-Met may, however, exhibit cross-reactivity to other antigens such as c-Met molecules from other species.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "effective amount" or "therapeutically effective amount" of an agent, e.g., a pharmaceutical formulation, refers to an amount effective, at dosages and for periods of time necessary, to achieve the desired therapeutic or prophylactic result.

As used herein, the term "treating" is used to refer to both prevention of a disease or disorder, and treatment of pre-existing or diagnosed conditions.

II. THERAPEUTIC METHODS USING AGONIST C-MET ANTIBODIES

A. c-Met as a Therapeutic Target

The c-Met receptor protein, also known as the hepatocyte growth factor (HGF) receptor, is expressed on the surface of epithelial cells of many organs, including the liver, pancreas, prostate, kidney, muscle and bone marrow. The ligand for c-Met is HGF. HGF acts as a pleiotropic factor and cytokine, promoting cell proliferation, survival, motility, scattering, differentiation and morphogenesis in various tissues of the body. In addition, HGF appears to play a protective role in several diseases, including liver cirrhosis, lung fibrosis, and progressive nephropathies. Upon binding of HGF to the c-Met extracellular domain, multiple tyrosine residues within the cytoplasmic domain of c-Met are phosphorylated. Phosphorylation of Y1234 and Y1235 activates c-Met tyrosine kinase activity and subsequent phosphorylation of the Y1349 and Y1356 residues (Matsumoto et al., 2014, Biomedicines, 2:275-300). Phosphorylated tyrosine residues recruit various intracellular signaling molecules resulting in biological activities such as promotion of mitogenesis and migration, suppression of cell death, and induction of epithelial morphogenesis. HGF-c-Met interaction has been shown to play a role in diverse biological systems including but not limited to the liver, kidney, skin, pancreas, lung, the nervous system, heart and immune system.

Disclosed herein are therapeutic compositions and methods for administering to a subject in need thereof a polypeptide which specifically binds the c-Met protein and which activates c-Met in a manner which may be similar to activation by binding of HGF. Data are provided below to show that the c-Met activating polypeptides disclosed herein are therapeutically effective in preventing or treating a variety of conditions indicative of disease states.

B. c-Met Agonist Antibodies

An immunoglobulin which binds the c-Met protein was generated as described in PCT Application No. PCT/KR2015/007899 (the contents of which are incorporated by reference in their entirety). In summary, a fully humanized single-chain antibody (scFv) phage display library for biopanning was used to select scFv species which bound human c-Met. The scFv referred to herein as "1E4" scFv was identified and demonstrated to bind c-Met with high affinity and has the amino acid sequence presented herein as SEQ ID NO:3. The 1E4 scFv or variants thereof can be used for treating a subject in need thereof as described in more detail below.

Also described in PCT/KR2015/007899 is the construction of a full-length immunoglobulin having the heavy chain variable domain (SEQ ID NO:1) and light chain variable domain (SEQ ID NO:2) of the 1E4 scFv, as well as human IgG light chain constant domain and human IgG heavy chain constant domains. The heavy chain variable domain comprises a CDR1 (SEQ ID NO:5), a CDR2 (SEQ ID NO:6) and a CDR3 (SEQ ID NO:7). The light chain variable domain comprises a CDR1 (SEQ ID NO:8), a CDR2 (SEQ ID NO:9), and a CDR3 (SEQ ID NO:10). The person having ordinary skill in the art understands that antigen binding specificity of an immunoglobulin is determined largely by the CDR sequences. Accordingly, in some embodiments, the presently disclosed methods encompass treatment with an antibody comprising a heavy chain variable domain comprising the CDRs of SEQ ID NO:5, SEQ ID NO:6 and SEQ ID NO:7, and a light chain variable domain comprising the CDRs of SEQ ID NO:8, SEQ ID NO:9 and SEQ ID NO:10. In additional embodiments, the antibody comprises an IgG heavy chain comprising SEQ ID NO:1 and an IgG light chain comprising SEQ ID NO:2. The amino acid sequences of the 1E4 constructs described above are presented in Table 1.

TABLE 1

| SEQ ID NO | Description | Sequence |
|---|---|---|
| 1 | Heavy chain variable domain | QVQLVQSGAEVKKPGESLRISCQGSGYSFPTHWIT WVRQMPGKGLEWMGTIDPTDSYNFYGPSFQGHVTI SADSSSSTAYLQWSSLKASDTAMYYCARDGNYYDS RGYYYDTFDMWGQGTLVTVSS |
| 2 | Light chain variable domain | DIQMTQSPSFLSASVGDRVTITCRASQGISTYLAW YQQKPGTAPKLLIYSASTLESGVPSRFSGSGSGTD FTLTISSLQPEDSATYYCQQADSFPLTFGGGTKVE IKRGGASLVE |
| 3 | 1E4 scFv | QVQLVQSGAEVKKPGESLRISCQGSGYSFPTHWIT WVRQMPGKGLEWMGTIDPTDSYNFYGPSFQGHVTI SADSSSSTAYLQWSSLKASDTAMYYCARDGNYYDS RGYYYDTFDMWGQGTLVTVSSGLGGLGGGGSGGGG SGGSSGVGSDIQMTQSPSFLSASVGDRVTITCRAS QGISTYLAWYQQKPGTAPKLLIYSASTLESGVPSR FSGSGSGTDFTLTISSLQPEDSATYYCQQADSFPL TFGGGTKVEIKRGGASLVE |
| 4 | scFv linker | GLGGLGGGSGGGGSGGSSGVGS |
| 5 | Heavy chain CDR1 | THWIT |
| 6 | Heavy chain CDR2 | TIDPTDSYNFYGPSFQG |
| 7 | Heavy chain CDR3 | DGNYYDSRGYYYDTFDM |
| 8 | Light chain CDR1 | RASQGISTYLA |
| 9 | Light chain CDR2 | SASTLES |
| 10 | Light chain CDR3 | QQADSFPLT |

The 1E4 antibody for use in the treatment methods described herein is optionally referred to herein as an agonist antibody because the 1E4 antibody has been shown to both induce scattering in MDCK-2 (Madin-Darby Canine Kidney epithelial Cells-2) and to induce c-Met phosphorylation (PCT/KR2015/007899).

The 1E4 antibody has also been shown to bind to both human c-Met and mouse c-Met. Specifically, BIAcore analysis of the 1E4-IgG antibody was performed (PCT/KR2015/007899) using both human and mouse c-MET. The binding results are presented below in Table 2.

TABLE 2

| Protein | Ka (1/Ms) | Kd (1/s) | KD (M) |
|---|---|---|---|
| Mouse c-Met | $2.58 \times 10^6$ | $1.59 \times 10^{-3}$ | $6.15 \times 10^{-10}$ |
| Human c-Met | $2.71 \times 10^6$ | $8.07 \times 10^{-4}$ | $2.98 \times 10^{-10}$ |

Accordingly, in some embodiments, a method for treating a subject is provided comprising administering to the subject an antibody which binds to a human c-Met protein with a KD less than or equal to about $3 \times 10^{-10}$ M or which binds to a mouse c-Met protein with a KD less than or equal to about $7 \times 10^{-10}$ M, wherein the antibody is an agonist of c-Met function.

Unless specifically indicated otherwise, the term "antibody," as used herein, shall be understood to encompass antibody molecules comprising two immunoglobulin heavy chains and two immunoglobulin light chains (i.e., "full antibody molecules") as well as antigen-binding fragments thereof (e.g., the term "antibody," as used herein, shall be understood to encompass polypeptides comprising a heavy chain variable domain and a light chain variable domain).

Accordingly, the term "antibody" as used herein may encompass the scFv construct or other immunoglobulin proteins. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding portion" of an antibody, or "antibody fragment", as used herein, refers to one or more fragments of an antibody that retain the ability to specifically bind to c-Met protein. An antibody fragment may include a Fab fragment, a F(ab')$_2$ fragment, a Fv fragment, a dAb fragment, a fragment containing a CDR, or an isolated CDR. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and (optionally) constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

As with full antibody molecules, antigen-binding fragments may be mono-specific or multi-specific (e.g., bi-specific). A multi-specific antigen-binding fragment of an antibody will typically comprise at least two different variable domains, wherein each variable domain is capable of specifically binding to a separate antigen or to a different epitope on the same antigen. Any multi-specific antibody format, including the exemplary bi-specific antibody formats disclosed herein, may be adapted for use in the context of an antigen-binding fragment of an antibody of the present invention using routine techniques available in the art.

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. In some embodiments, an anti-c-Met antibody as used according to the methods described herein comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:1. In certain embodiments, a VH sequence having at least 90%, 91%, 92%, 93%, 94%, 95%, 96%, 97%, 98%, or 99% identity to SEQ ID NO:1 contains substitutions (e.g., conservative substitutions), insertions, or deletions relative to the reference sequence, but an anti-c-Met antibody comprising that sequence retains the ability to bind to c-Met. In certain embodiments, the substitutions, insertions, or deletions occur in regions outside the CDRs (i.e., in the framework regions). Optionally, the anti-c-Met antibody described comprising the VH sequence includes post-translational modifications of that sequence.

In another aspect, an anti-c-Met antibody as used according the methods described herein comprises a light chain variable domain (VL) having at least 90%, 91%, 92%, 93%, 94%, 95%, 96%, 97%, 98%, 99%, or 100% sequence identity to the amino acid sequence of SEQ ID NO:2. In certain embodiments, a VL sequence having at least 90%, 91%, 92%, 93%, 94%, 95%, 96%, 97%, 98%, or 99% identity to SEQ ID NO:2 contains substitutions (e.g., con/servative substitutions), insertions, or deletions relative to the reference sequence, but an anti-c-Met antibody comprising that sequence retains the ability to bind to c-Met. In certain embodiments, the substitutions, insertions, or deletions occur in regions outside the CDRs (i.e., in the framework regions). Optionally, the anti-c-Met antibody described comprising the VL sequence includes post-translational modifications of that sequence.

In some embodiments, an anti-c-Met antibody as used according to the methods described herein comprises a VH sequence having at least 90%, 91%, 92%, 93%, 94%, 95%, 96%, 97%, 98%, or 99% identity to SEQ ID NO:1 and a VL sequence having at least 90%, 91%, 92%, 93%, 94%, 95%, 96%, 97%, 98%, or 99% identity to SEQ ID NO:2, wherein the antibody specifically binds a c-Met protein having the sequence of SEQ ID NO:13. In other embodiments, the antibody binds to the c-Met protein having the sequence of SEQ ID NO:13 with $K_D$ less than or equal to about $3 \times 10^{-10}$ M. In still other embodiments, the antibody binds to the c-Met protein having the sequence of SEQ ID NO:15 with $K_D$ less than or equal to about $7 \times 10^{-10}$ M.

Any combination of deletion, insertion, and substitution can be made to arrive at the final construct, provided that the final construct possesses the desired characteristics, e.g., antigen-binding.

In certain embodiments, antibody variants having one or more amino acid substitutions are provided. Sites of interest for substitutional mutagenesis include the variable regions including the framework regions. Conservative substitutions are shown in Table 3 under the heading of "conservative substitutions." More substantial changes are provided in Table 3 under the heading of "Preferred substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 3

| Original Residue | Conservative Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, lie;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties. Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Antibody variants with at least one galactose residue in the oligosaccharide attached to the Fc region are also provided.

C. Generating 1E4 Immunoglobulins for Therapeutic Use

The generation of a full-length human 1E4 IgG antibody from the heavy and light chain variable domains of an scFv construct (SEQ ID NO:3) is done using routine methods and compositions. Construction of the human 1E4 antibody used in the methods described herein is described in Example 1 below and in PCT/KR2015/007899. The nucleic acids encoding variable domains of the 1E4 antibody as described herein (SEQ ID NOS: 11 and 12 and variants thereof) can be used to generate full-length antibodies using routine methods. In some embodiments, a nucleic acid encoding a heavy chain of an anti-c-Met antibody of the present disclosure can comprise a nucleotide sequence encoding a VH domain of the disclosure (SEQ ID NO:11) joined in-frame to a nucleotide sequence encoding a heavy chain constant domain from any source. Similarly, a nucleic acid molecule encoding a light chain of an anti-c-Met antibody of the present disclosure can comprise a nucleotide sequence encoding a VL domain of the disclosure (SEQ ID NO:12) joined in-frame to a nucleotide sequence encoding a light chain constant domain from any source.

In a further aspect of the disclosure, nucleic acid molecules encoding the variable domain of the heavy (VH) and/or light (VL) chains are "converted" to full-length antibody genes. In one embodiment, nucleic acid molecules encoding the VH or VL domains are converted to full-length antibody genes by insertion into an expression vector already encoding heavy chain constant (CH) or light chain constant (CL) domains, respectively, such that the VH segment is operatively linked to the CH segment(s) within the vector, and/or the VL segment is operatively linked to the CL segment within the vector. In another embodiment, nucleic acid molecules encoding the VH and/or VL domains are converted into full-length antibody genes by linking, e.g., ligating, a nucleic acid molecule encoding a VH and/or VL domains to a nucleic acid molecule encoding a CH and/or CL domain using standard molecular biological techniques. Nucleic acid sequences of human heavy and light chain immunoglobulin constant domain genes are known in the art. See, e.g., Kabat et al., Sequences of Proteins of Immunological Interest, 5th Ed., NIH Publ. No. 91-3242, 1991. Nucleic acid molecules encoding the full-length heavy and/or light chains may then be expressed from a cell into which they have been introduced and the anti-c-Met antibody isolated.

The nucleic acid molecules may be used to recombinantly express large quantities of anti-c-Met antibodies. The nucleic acid molecules also may be used to produce chimeric antibodies, bispecific antibodies, single chain antibodies, immunoadhesins, diabodies, mutated antibodies and antibody derivatives, as described further above.

Similarly, in some embodiments, the polynucleotides encoding the heavy chain variable domain (SEQ ID NO:1) and the light chain variable domain (SEQ ID NO:2) can be joined by a polynucleotide encoding a linker (e.g., SEQ ID NO:4), cloned into an expression vector and expressed from a cell into which the vector has been introduced to produce an scFv construct for use in the treatment methods described herein.

D. Wound Healing

In one aspect, a method for promoting wound healing in a subject in need thereof is provided comprising administering to the subject a therapeutically effective amount of a polypeptide comprising the heavy and light chain variable domains of the 1E4 antibody as described herein. As described in Example 2 below, administration of 1E4 antibody to the wounds of a mouse resulted in a faster wound healing time as compared to healing of wounds in mice not administered the 1E4 antibody. As shown in FIG. 1, topical administration to a skin wound on a mouse of 3 µg, 6 µg or 12 µg of 1E4 antibody was effective in reducing wound area by at least 20% as compared to healing in the absence of 1E4 immunoglobulin. A skilled artisan would thereby understand that administration of an immunoglobulin molecule comprising the c-Met binding domains of 1E4 would be effective in promoting wound healing in a subject.

Wound healing has been shown to require the HGF-c-Met pathway. Wounds can occur from many sources, including a break in the skin or other tissue or organ, such as lacerations, cuts, scrapes, blisters, abrasions, burns, diabetic ulcers, bedsores, surgical wounds, and other wounds. All wounds regardless of their nature undergo a similar process of wound healing. Wound healing occurs in four distinct phases. The first phase is blood clotting (hemostasis) when platelets arrive at the site of the wound where they are activated to promote clotting. The second phase, the inflammatory phase, is characterized by inflammation at the site of the trauma. This phase is critical for healing and involves extensive cell migration. The third phase of wound healing is the proliferative phase, which is marked by epithelialization, angiogenesis, granulated tissue formation and collagen deposition. Angiogenesis, which involves new capillary formation, is used to deliver nutrients and maintain granulation. Without formation of new capillaries into the wound, required nutrients fail to reach the wound resulting in a chronically unhealed wound. The fourth and final stage of wound healing is the maturational phase wherein fibroblasts differentiate into collagen. The compositions and methods of this disclosure are effective in one or more distinct phases of the wound healing. In one embodiment, the compositions and methods of the present disclosure trigger the proper healing sequence required in all forms of wounds and therefore prevent the destructive biochemical reactions typically brought on by a wound.

In one embodiment, the 1E4 antibody of the disclosure is effective against burn. There are various types of burn such as thermally induced burns, thermally induced controlled burns, chemical burns, radiation burns, electrical burns, ice burns, or burns caused by exposure to lightening that may be prevented and/or treated with the compositions and methods of the present disclosure. There are various degrees of burns including those that are 1st degree, 2nd degree, 3rd degree, or 4th degree burns or any combination thereof.

In another embodiment, the compositions and methods of the present disclosure directly or indirectly prevent microorganisms from invading the wound site by promoting wound healing. Patients will therefore also suffer less because they remain free from various infections commonly associated with typical wound. The composition thus prevents wound injuries from progressing to greater severity. The use of compositions and methods of the present disclosure prevents, treats and/or ameliorates the tissue damage that is the breeding ground for microorganisms in most wounds. The ability to interfere with the cycle of infection can halt the disease process. The reduced rate of infection translates to reduced severity of disease, disorders and deformities that are normal consequences of a wound.

Other conditions related to wounds or sores which may be successfully treated or prevented according to the disclosure are, by way of example and not limitation, anthrax wounds, tetanus, gas gangrene, scalatina, erysipelas, sycosis barbae, folliculitis, impetigo contagiosa, or impetigo bullosa, etc.

In practicing the method of treatment or use of the present disclosure, a therapeutically effective amount of an agonist c-Met immunoglobulin is administered to a subject in need of wound healing. The immunoglobulin may be administered in accordance with the method of the present disclosure either alone or in combination with other known therapies. When co-administered with one or more other therapies, the immunoglobulin may be administered either simultaneously with the other treatment(s), or sequentially. If administered sequentially, the attending physician will decide on the appropriate sequence of administration, which may be before or after a second therapy.

E. Prevention or Treatment of Damage to Kidney Tissue

Figure 2A:
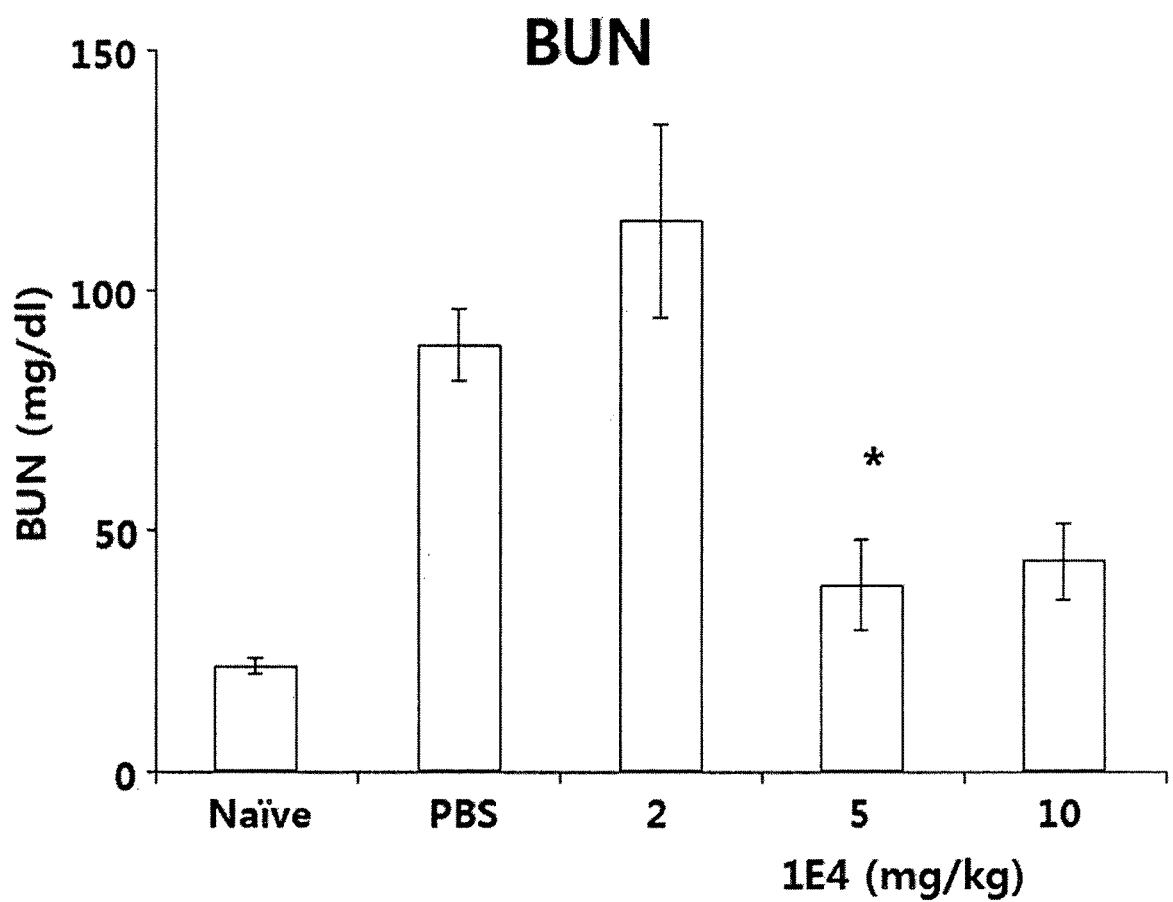
FIGS. 2A-2B show a protective effect of an agonist anti-c-Met antibody in the adriamycin (ADR)-induced nephropathy model.
Figure 2B:
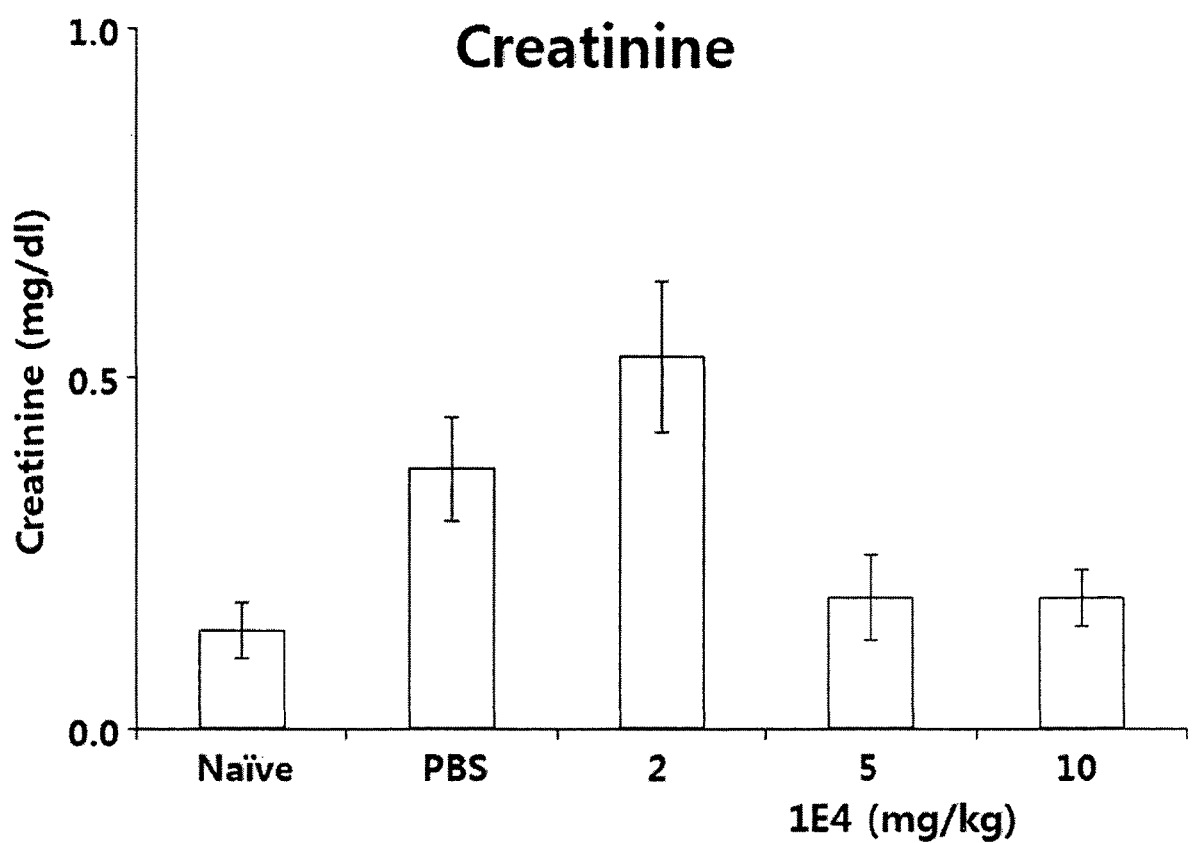

In one aspect, methods for preventing or treating damage to kidney tissue is provided comprising administering to a subject in need thereof a polypeptide comprising the variable domains of the 1E4 antibody as described herein. Experiments were done as described in Example 3 below to show that administration of the 1E4 antibody to an animal reduces kidney tissue damage which is caused by administration to the animal of the chemotherapeutic drug adriamycin (ADR). Specifically, BALB/c mice were treated with 2 mg/kg, 5 mg/kg or 10 mg/kg 1E4 antibody by tail vein injections. The following day, kidney injury was induced by a single tail injection of 15 mg/kg ADR. The mice were then injected intravenously with 2 mg/kg, 5 mg/kg or 10 mg/kg 1E4 antibody 2 and 5 days after injection of the ADR. As the data in FIGS. 2A and 2B show, doses of 5 mg/kg or more of 1E4 immunoglobulin are effective in reducing the increased levels of BUN (blood urea nitrogen) and creatinine. Increasing BUN and creatinine levels in the blood are indicative of kidney malfunction and damage. Plasma concentrations of creatinine and urea (which are highly dependent on glomerular filtration) begin a nonlinear rise as the renal function diminishes. Changes in creatinine and urea concentrations are minimal early on; later levels increase rapidly and are usually associated with systemic manifestations.

After administration of ADR, animals treated with PBS only experienced increases in both BUN and creatinine (FIGS. 2A and 2B, "PBS" as compared to "naïve" animals which were not treated with ADR or antibody). However, administration of 5 mg/kg or 10 mg/kg 1E4 antibody resulted in decreased levels of both BUN and creatinine as compared to levels in animals not treated with 1E4 antibody. Moreover, significant reduction of kidney tissue damage in the presence of at least 5 mg/kg of 1E4 immunoglobulin was observed via histological analysis (see Example 3).

Renal fibrosis results from an excessive accumulation of extracellular matrix that occurs in almost every type of chronic kidney disease and ultimately leads to end-stage renal failure. Renal fibrosis is thought by some as a failed wound-healing process of the kidney tissue after chronic, sustained injury. Example 4 below describes use of an animal model for renal fibrosis and shows that administration of the 1E4 antibody decreased the extent of fibrotic lesions in the kidney tissue. Accordingly, in some embodiments is a method for treating or preventing damage to kidney tissue comprising administering a 1E4 immunoglobulin.

The methods and compositions of the present disclosure are applicable to the treatment and prevention of various renal diseases and renal injury, both primary and secondary. Secondary renal diseases include those diseases resulting from a pre-existing condition such as diabetes or hypertension. The methods and compositions of the present invention find application particularly in chronic inflammatory and autoimmune diseases characterized by pathological changes of tubulointerstitial nephropathy or glomerulonephropathy and by proteinuria. Diseases include, but are not limited to, focal segmental glomerulosclerosis, glomerulonephritis, diabetic renal disease, hypertensive renal disease, renal failure, End Stage Renal Disease, and related conditions.

Additionally, chronic renal failure may result from any major cause of renal dysfunction. The most common cause of end-stage renal disease is diabetic nephropathy, followed by hypertensive nephroangiosclerosis and various primary and secondary glomerulopathies. Other causes include but are not limited to glomerulopathies, e.g. IgA nephropathy, focal glomerulosclerosis, membranous nephropathy, membranoproliferative glomerulonephritis, idiopathic crescentic glomerulonephritis, diabetes mellitus, postinfectious glomerulonephritis, systemic lupus erythematosus, Wegener's granulomatosis, hemolytic-uremic syndrome, amyloidosis; chronic tubulointerstitial nephropathies; hereditary nephropathies, e.g. polycistic kidney disease, Alport's syndrome, medullary cystic disease, Nail-patella syndrome; hypertension, e.g. nephroangiosclerosis, malignant glomerulosclerosis; renal macrovascular disease; and obstructive uropathy, e.g. ureteral obstruction, vesicoureteral reflux, benign prostatic hyperplasia; and the like.

In practicing the method of treatment or use of the present disclosure, a therapeutically effective amount of an agonist c-Met immunoglobulin is administered to a subject afflicted with a disease or disorder related to loss of renal function. The immunoglobulin may be administered in accordance with the method of the present disclosure either alone or in combination with other known therapies. When co-administered with one or more other therapies, the immunoglobulin may be administered either simultaneously with the other treatment(s), or sequentially. If administered sequentially, the attending physician will decide on the appropriate sequence of administration, which may be before or after a second therapy.

F. Treatment or Prevention of Tissue Damage Due to Ischemia

In one aspect, methods for preventing or treating ischemic damage to tissue is provided comprising administering to a subject in need thereof a polypeptide comprising the variable domains of the 1E4 antibody as described herein. The 1E4 antibody was shown to be effective for reducing injury due to ischemic stroke in an animal model (see Example 5). An animal model was used in which the middle cerebral artery was occluded in rats which had been administered 10 mg/kg 1E4 antibody 1 day earlier. The rats were then intravenously administered 10 mg/kg 1E4 antibody 1 hour after on days 3, 10, 17 and 24 after occlusion. Analysis of brain tissue was performed using an MRI to measure the extent of infarction. The results showed that administration of the 1E4 antibody was effective in reducing infarction size in the occlusion model (see FIG. 5).

Ischemia refers to a reduction or abolition of blood supply to a tissue. The immunoglobulin polypeptides and methods described herein can be used to treat injuries associated with ischemia, or "ischemic injuries." Ischemic injuries can include injuries to, e.g., the kidney, liver, lungs, pancreas, skeletal muscle, intestines, heart and brain. Ischemic injuries can be associated with or caused by, e.g., stroke, acute myocardial infarction, elective angioplasty, coronary artery bypass graft, surgery involving cardiac bypass or organ or tissue transplantation (e.g., cardiac transplantation), tissue rejection after transplantation, graft versus host disease, head trauma, drowning, sepsis, cardiac arrest, shock, atherosclerosis, hypertension, cocaine-induced heart disease, smoking-induced heart disease, heart failure, pulmonary hypertension, hemorrhage, capillary leak syndrome (such as child and adult respiratory distress syndrome), multi-organ system failure, a state of low colloid oncotic pressure (such as starvation, anorexia nervosa, or hepatic failure with decreased production of serum proteins), anaphylaxis, hypothermia, cold injury (e.g., due to hypothermic perfusion or frostbite) hepatorenal syndrome, delirium tremens, a crush injury, mesenteric insufficiency, peripheral vascular disease, claudication, burn, electrocution, excessive drug-induced vasodilation, excessive drug-induced vasoconstriction, radiation exposure (e.g., during fluoroscopy or radiographic imaging), or exposure to high energy, e.g., exposure to laser light. Excessive drug-induced vasodilation can be caused by, for instance, nitroprusside, hydralazone, dyazoxide, a calcium channel blocker, or a general anesthetic. Excessive drug-induced vasoconstriction can be caused by, for instance, neosynephrine, isoproterenol, dopamine, dobutamine, or cocaine.

Stroke is a general term for acute brain damage resulting from disease or injury of blood vessels. Stroke can be classified into at least two main categories: hemorrhagic stroke (resulting from leakage of blood outside of the normal blood vessels) and ischemic stroke (cerebral ischemia due to lack of blood supply). Some events that can cause ischemic stroke include thrombosis, embolism, and systemic hypoperfusion (with resultant ischemia and hypoxia). Stroke generally causes neuronal death and injury in the brain by oxygen deprivation and secondary events. The area of the brain that dies as a result of the lack of blood supply or other damage is called an infarct. In some cases, the treatments described herein can be used to reduce or minimize the size of an infarct, e.g., by reducing secondary events that cause neuronal death or injury.

Obstruction of a cerebral artery resulting from a thrombus which has built up on the wall of a brain artery is generally called cerebral thrombosis. In cerebral embolism, the occlusive material blocking the cerebral artery arises downstream in the circulation (e.g., an embolus is carried to the cerebral artery from the heart). Because it is difficult to discern whether a stroke is caused by thrombosis or embolism, the term thromboembolism is used to cover both these types of stroke. Systemic hypoperfusion may arise as a consequence of decreased blood levels, reduced hematocrit, low blood pressure or inability of the heart to pump blood adequately.

In practicing the method of treatment or use of the present disclosure, a therapeutically effective amount of an agonist c-Met immunoglobulin is administered to a subject afflicted with a disease or disorder related to ischemia. The immunoglobulin may be administered in accordance with the method of the present disclosure either alone or in combination with other known therapies. When co-administered with one or more other therapies, the immunoglobulin may be administered either simultaneously with the other treatment(s), or sequentially. If administered sequentially, the attending physician will decide on the appropriate sequence of administration, which may be before or after a second therapy.

G. Treatment of Pathologic Retinal Neovascularization

In one aspect, methods for preventing or treating a neovascular retinal disease related to pathologic neovascularization in the retina is provided comprising administering to a subject in need thereof a polypeptide comprising the variable domains of the 1E4 antibody as described herein. Example 6 below describes the successful treatment of pathologic neovascularization in an animal model. Specifically, a laser-induced choroidal neovascularization model (CNV) was used with Chinchilla rabbits in which photocoagulation spots were created around the optic nerve. Treatment of the rabbits with 50 µg 1E4 antibody by direct administration to the vitreous humor resulted in inhibition of laser-induced CNV formation (see FIG. 6), supporting embodiments in which a subject in need thereof is treated with 1E4 immunoglobulin compositions for the treatment or prevention of pathologic neovascularization in the retina.

The pathologic growth of new blood vessels (neovascularization) in and around the tissues of the eye is associated with a variety of ocular diseases. In particular, hypoxia is known to be the primary stimulus for pathologic neovascularization of the choroid and Bruch's membrane that results in the often catastrophic vision loss associated with diabetic retinopathy, retinopathy of prematurity, and the wet form of AMD.

Disclosed herein are methods for the treatment of diseases or conditions of the eye, especially retinopathies, ocular edema and ocular neovascularization. Non-limiting examples of these diseases or conditions include diabetic macular edema, age-related macular degeneration (wet form), choroidal neovascularization, diabetic retinopathy, ocular ischemia, uveitis, retinal vein occlusion (central or branch), ocular trauma, surgery induced edema, surgery induced neovascularization, cystoid macular edema, ocular ischemia, uveitis, and the like. These diseases or conditions are characterized by changes in the ocular vasculature whether progressive or non-progressive, whether a result of an acute disease or condition, or a chronic disease or condition. In other embodiments, the subject is suffering from ischemia-induced neovascularization. Ischemia-induced neovascularization need not necessarily be caused by disease. For example, injury or insult to the ocular tissue can lead to hypoxia of ocular tissues and thereby cause ischemia-induced neovascularization which results in loss of vision.

One aspect of the disclosed methods relates to diseases that are a direct or indirect result of diabetes, including diabetic macular edema and diabetic retinopathy. Another condition that may occur is non-proliferative retinopathy in which vascular changes, such as microaneurysms, may occur outside the macular region of the eye. These conditions may or may not progress to diabetic proliferative retinopathy which is characterized by neovascularization. Typically, subjects having diabetic macular edema are suffering from the non-proliferative stage of diabetic retinopathy; however, it is not uncommon for subjects to only begin manifesting macular edema at the onset of the proliferative stage.

In practicing the method of treatment or use of the present disclosure, a therapeutically effective amount of an agonist c-Met immunoglobulin is administered to a subject afflicted with a disease or disorder related to pathologic retinal neovascularization. The immunoglobulin may be administered in accordance with the method of the present disclosure either alone or in combination with other known therapies. When co-administered with one or more other therapies, the immunoglobulin may be administered either simultaneously with the other treatment(s), or sequentially. If administered sequentially, the attending physician will decide on the appropriate sequence of administration, which may be before or after a second therapy.

H. Treatment of Neuronal Diseases

In one aspect, methods for preventing or treating a neuronal disease or disorder is provided comprising administering to a subject in need thereof a polypeptide comprising the variable domains of the 1E4 antibody as described herein. Activation of c-Met by binding of HGF plays a role in development and maintenance of the nervous system, as c-Met is expressed in developing and adult brains including neurons of the cerebral cortex, hippocampus, cerebellum, brainstem motor nucleus, retina and sensory ganglia, and the spinal cord, as well as non-neuronal cells such as reactive astrocytes, oligodendrocyte progenitors, oligodendrocytes, and microglia (see Funakoshi and Nakamura, 2011, Current Signal Transduc Ther, 6:156-167 for review).

Figure 7A:
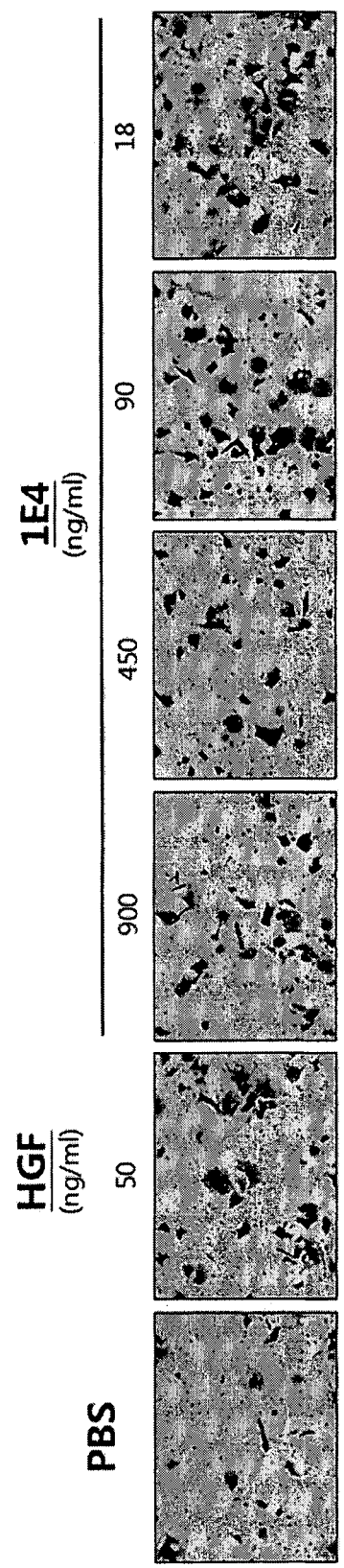
FIGS. 7A and 7B show migrating-promoting effects of an agonist anti-c-Met antibody on Schwann cells (iSc) in a Transwell assay.
Figure 7B:
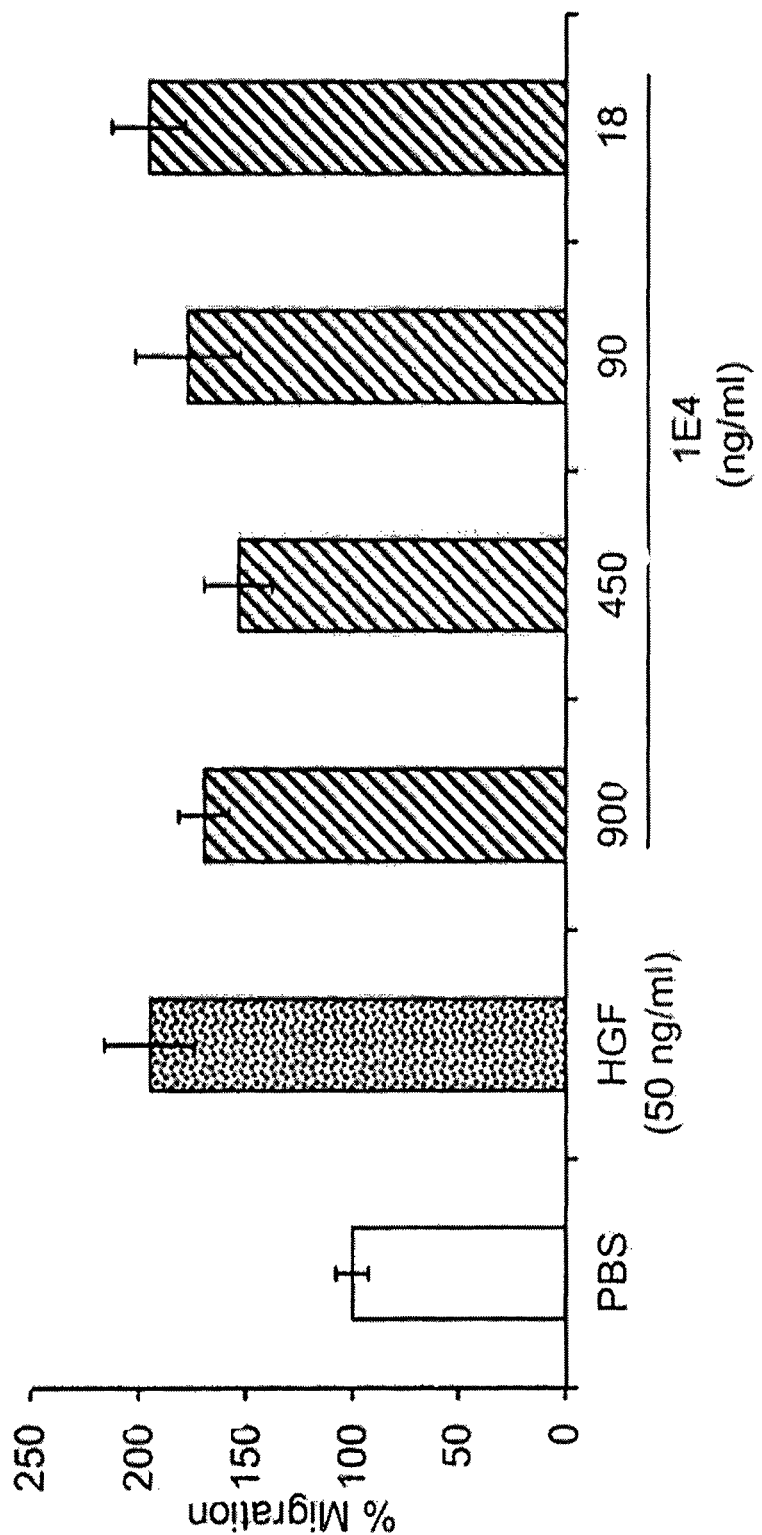

Experiments described in Example 7 were done to study the effects of 1E4 agonist antibody administration on Schwann cell migration. Schwann cells are known to play important roles in nervous system development, function and maintenance. For example, re-myelination of damaged nerves requires migration of Schwann cells to the damaged nerves. As demonstrated in Example 7 and shown in FIGS. 7A and 7B, administration of 1E4 antibody to rat Schwann cells in culture significantly increased the migration activity of these cells as compared to cells treated only with buffer.

Figure 8A:
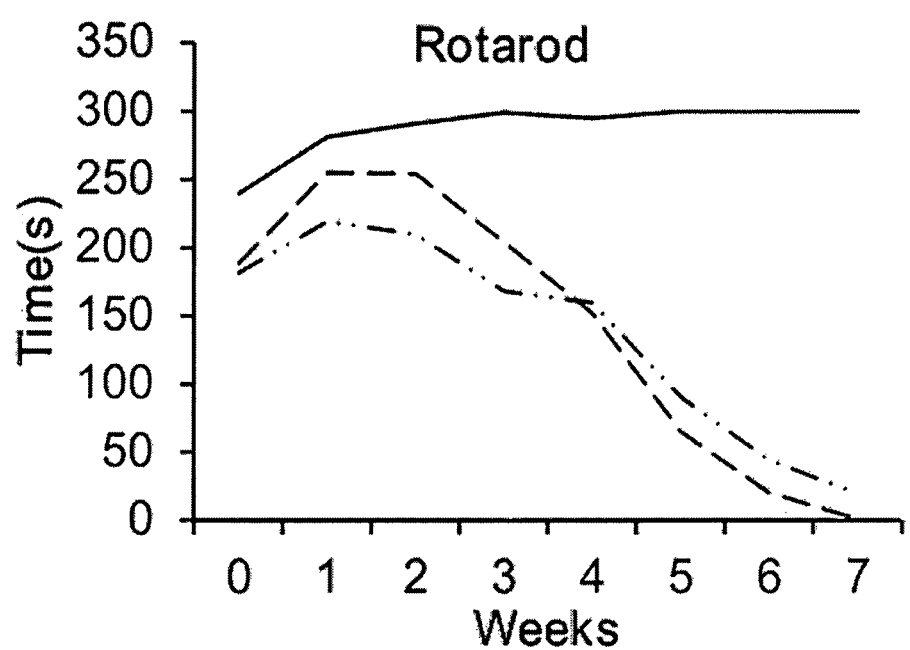
FIGS. 8A-8D illustrate the effects of an agonist anti-c-Met antibody on motor function and survival of B6SJL-Tg (SOD1-G93A) mice. Results are shown for weekly assessment of Rotarod (FIG. 8A), grip strength (FIG. 8B), body weight (FIG. 8C), and survival (FIG. 8D).
Figure 8B:
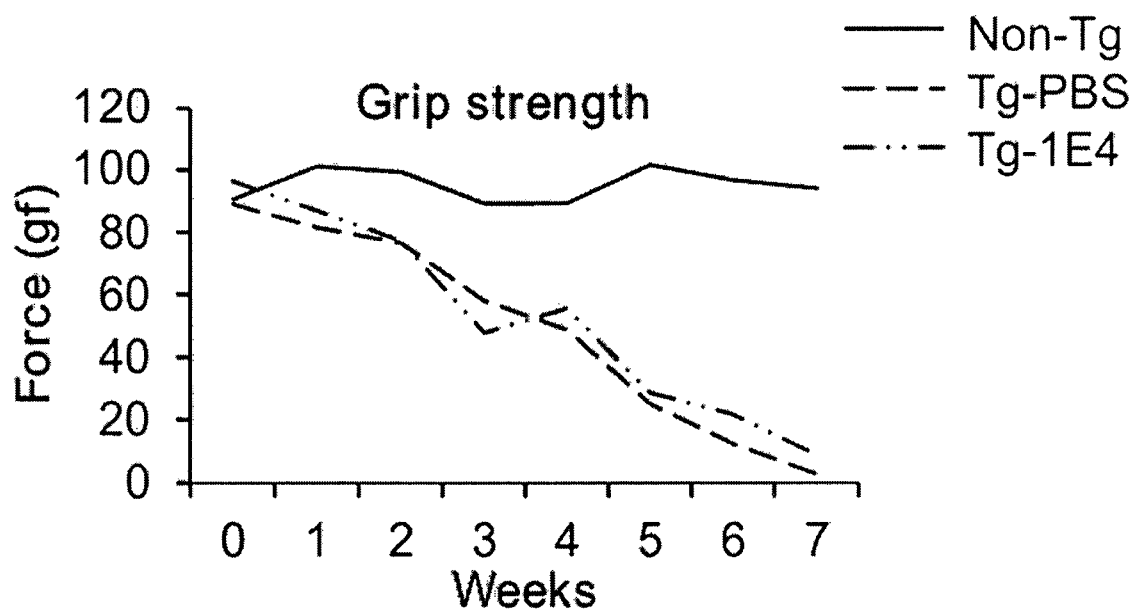
Figure 8C:
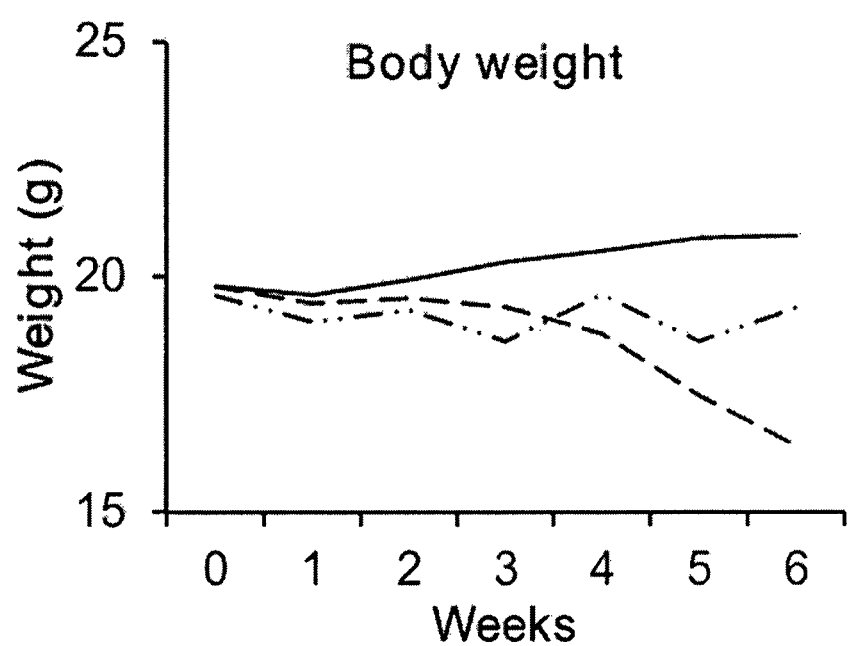
Figure 8D:
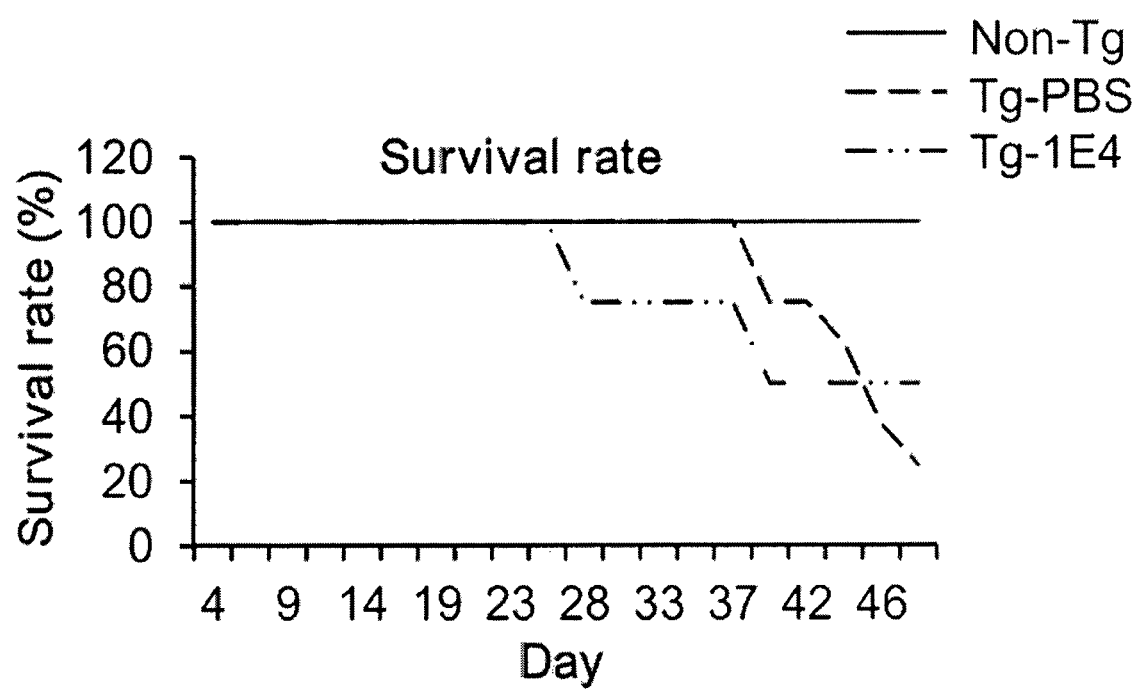

The effects of an agonist c-Met antibody as disclosed herein were further studied using an animal model for amyotrophic lateral sclerosis. B6SJL-Tg (SOD1-G93A) mice expressing human mutant SOD1 are accepted as an animal model to study the therapeutic effect of agents on ALS and other neuromuscular diseases. Mice treated with 1E4 antibody intrathecally and intraperitoneally as described in Example 8 were found to have improved motor function when administered 1E4 antibody as compared to mice administered buffer alone (FIGS. 8A and 8B). 1E4 antibody treatment also improved survival rates (FIG. 8D).

The experimental data provided in Examples 7 and 8 show that compositions comprising agonist c-Met antibodies as described herein can be used to treat subjects suffering from disorders involving neurological cells.

The potential role of HGF and c-Met in neuronal systems have been summarized in Funakoshi and Nakamura, 2011, Current Signal Transduc Ther, 6:156-167. As an example, studies have shown the following. Mutations in the HGF and c-Met genes have been associated with autism, schizophrenia and nonsyndromic hearing loss. Increased serum HGF levels have been associated with efficacy of antidepressant therapy in patients with panic disorder. HGF has been shown to act as a potent cerebroprotective agent for functional recovery after ischemic brain injuries. HGF has been shown to prevent neuronal cells death by inhibiting apoptosis. HGF has been shown to have beneficial effects on motor neurons in vitro and in vivo and such effects have been considered as indicative of potential therapeutic value in treating amyotrophic lateral sclerosis (ALS). Beneficial effects have been reported for various studies which increased HGF levels in the hippocampus of animals suggesting a therapeutic role for a c-Met agonist in treating Alzheimer's disease. Additionally, neurotrophic effects of HGF in primary midbrain dopaminergic neurons and beneficial effects of a c-Met agonist on Parkinson's disease have been reported. Application of exogenous HGF genes into the injured spinal cord promoted survival of motor neurons and reduced the size of damaged area supporting the potential use of a c-Met agonist antibody to treat spinal cord injury.

As activation of c-Met has been associated with a diverse array of beneficial effects on neuronal disease or damage, In practicing the method of treatment or use of the present disclosure, a therapeutically effective amount of an agonist c-Met immunoglobulin is administered to a subject afflicted with an indication which is a neuronal disease, disorder, or injury. Such indications include but are not limited to ischemic brain injury, Alzheimer's disease, Parkinson's disease, amyotrophic lateral sclerosis, spinal cord injury, multiple sclerosis, seizure, hydrocephalus, retinal injury, hearing impairment, peripheral nerve injury and neuropathy, and neuropathic pain.

I. Pharmaceutical Compositions

In a further aspect, the present disclosure provides a pharmaceutical composition comprising an antibody or a conjugate thereof and a pharmaceutically acceptable carrier.

In some embodiments, a pharmaceutical composition for treating an ischemic disorder, a stroke, a kidney injury or disease, a retinal neovascularization disorder, a neurological disorder or disease, or a wound, comprising an antibody or fragment thereof which binds to c-Met (mesenchymal-epithelial transition factor) as an active ingredient and a pharmaceutically acceptable carrier is provided, wherein the antibody comprises: an heavy chain variable domain which comprises a CDR1 of SEQ ID NO:5, a CDR2 of SEQ ID NO:6, and a CDR3 of SEQ ID NO:7; and an light chain variable domain which comprises a CDR1 of SEQ ID NO:8, a CDR2 of SEQ ID NO:9 and a CDR3 of SEQ ID NO:10.

In some embodiments, the heavy chain variable domain comprises SEQ ID NO:1 and the light chain variable domain comprises SEQ ID NO:2.

In some embodiments, a pharmaceutical composition for treating an ischemic disorder, a stroke, a kidney injury or disease, a retinal neovascularization disorder, a neurological disorder or disease, or a wound, comprising a scFv which binds to c-Met as an active ingredient and a pharmaceutically acceptable carrier is provided, wherein the scFv comprises: an heavy chain variable domain comprises SEQ ID NO:1 and the light chain variable domain comprises SEQ ID NO:2.

In some embodiments, the scFv comprises SEQ ID NO:3.

The pharmaceutical composition can be brought into contact with the body through diverse administration routes, including intravenous administration, intramuscular administration, intra-arterial administration, intramedullary administration, intrathecal administration, intracardiac administration, intravitreal administration, percutaneous administration, hypodermic administration, intraperitoneal administration, sublingual administration, subcutaneous, transdermal, and topical administration.

For such clinical administration, the pharmaceutical composition of the present invention can be prepared in an adequate product using conventional techniques.

Pharmaceutical formulations of an anti-c-Met antibody as described herein are prepared by mixing such antibody having the desired degree of purity with one or more optional pharmaceutically acceptable carriers (Remington's Pharmaceutical Sciences 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH2O (HYLENEX®, Baxter International, Inc.). Certain exemplary sHASEGPs and methods of use, including rHuPH$_2$O, are described in US Patent Publication Nos. 2005/0260186 and 2006/0104968. In one aspect, a sHASEGP is combined with one or more additional glycosaminoglycanases such as chondroitinases.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

For better administration, the composition can further comprise at least one kind of pharmaceutically acceptable carrier in addition to the above-described active ingredients. Examples of such carriers include saline solution, sterile water, Ringer's solution, buffered saline solution, dextrose solution, maltodextrin (aqueous) solution, glycerol, ethanol and mixtures thereof. If needed, typical additives, such as, an antioxidant, a buffer, a bacteriostatic agent and the like, can be added. Moreover, the composition can be pharmaceutically produced for injection in the form of an aqueous solution, suspension, emulsion and so forth by adding more additives, such as, a diluting agent, a dispersing agent, a surfactant, a bonding agent and a lubricant.

J. Dosing

Effective dosages and schedules for administering the 1E4 c-Met antibody may be determined empirically, and making such determinations is within the skill in the art. Those skilled in the art will understand that the dosage of the agent that must be administered will vary depending on, for example, the subject which will receive the agent, the route of administration, the particular type of agent used and other drugs being administered to the subject. For example, guidance in selecting appropriate doses for antibodies is found in the literature on therapeutic uses of antibodies, e.g., Handbook of Monoclonal Antibodies, Ferrone et al., eds., Noges Publications, Park Ridge, N.J., (1985) ch. 22 and pp. 303-357; Smith et al., Antibodies in Human Diagnosis and Therapy, Haber et al., eds., Raven Press, New York (1977) pp. 365-389. A typical dose of the agent used alone might range from about 0.01 mg/kg to up to 500 mg/kg of body weight or more per day, or from about 0.01 mg/kg to about 50 mg/kg, or from 0.1 mg/kg to about 50 mg/kg, or from about 0.1 mg/kg to up to about 10 mg/kg, or from about 0.1 mg/kg to up to about 5 mg/kg, or from about 5 mg/kg to up to about 10 mg/kg or from about 0.2 mg/kg to about 1 mg/kg, depending on the factors mentioned above.

The dosing schedules for administration of a 1E4 antibody include, but are not limited to, once daily, three-times weekly, twice weekly, once weekly, three times, twice monthly, once monthly and once every other month.

IV. EXAMPLES

The following examples are illustrative in nature and are in no way intended to be limiting.

Example 1

Preparation of a c-Met Antibody

The 1E4 IgG1 antibody used in the Examples below was generated by recombinant expression in HEK-293T cells. A pIgGHD vector (Aprogen, South Korea) was constructed to contain the nucleic acid encoding the full-length 1E4 antibody heavy chain and a separate pIgGLD vector (Aproge, South Korea) was constructed to contain the nucleic acid encoding the full-length 1E4 antibody light chain. The nucleic acids encoding the heavy and light chain variable domains of the 1E4 antibody had been obtained from ScFv polypeptides generated by biopanning of a phage display library. This generation of the 1E4 heavy and light chain variable domains is described in PCT Application No. PCT/KR2015/007899, the contents of which are incorporated herein by reference in their entirety. The 1E4 light chain variable domain has the amino acid sequence described herein as SEQ ID NO:2 and the 1E4 heavy chain variable domain has the amino acid sequence described herein as SEQ ID NO:1. The nucleic acid encoding the 1E4 light chain variable domain was ligated to the pIgGLD vector which had been digested with the SfiI endonuclease, and the nucleic acid encoding the 1E4 heavy chain variable domain was ligated to the pIgGHD vector which had been digested with the SfiI endonuclease. recombinantly express the full length 1E4 antibody used for the examples below, the pIgGHD vector was digested with the SfiI endonuclease and the pIgGLD vector was digested with the BstXI endonuclease. To produce the 1E4 IgG antibody, HEK-293T cells were co-transfected with equal amounts of the light chain and heavy chain expression vectors.

The co-transfected cells were incubated in serum free medium free style 293 media (37'C, 5% $CO_2$) then the media was collected. 1E4 IgG antibody was purified from the media supernatant by protein A affinity chromatography (GE healthcare, US), following the manufacturer's protocol: the supernatant was equilibrated with 20 mM sodium phosphate (pH 7.0) and 100 mM NaCl, injected into a protein A column, the column was washed with 20 mM sodium phosphate (pH 7.0), 1 mM EDTA, 500 mM NaCl, then the antibody was eluted from the column with 0.1 M Glycine-HCl (pH 3.3) containing 100 mM NaCl. The eluted protein was neutralized with 1M Tris solution. The neutralized protein was then mixed with 5 mM sodium phosphate (pH 6.0) at a 1:1 ratio then injected into a prepacked SP-sepharose column (GE healthcare) equilibrated with 5 mM sodium phosphate (pH 6.0) containing 50 mM NaCl. The column-bound protein was eluted using sodium phosphate buffer (pH 7.0) containing 50 mM NaCl, and the unbound protein was obtained from a prepacked Q-sepharose column (GE healthcare) that had been equilibrated with release buffer. The protein eluate was concentrated with 30 kDa vivaspin20 (Sartorius) and dialyzed with PBS.

Example 2

Effects of Anti c-Met Agonist Antibodies on Wound Healing

The ability of the 1E4 antibody to promote wound healing in an animal was studied. Under sterile condition, mice (Balb/C, 8-week-old female) were anesthetized. After depilation of the dorsal fur, 6 mm circular wounds were made on either side of the dorsal skin of the mice using a 6 mm biopsy punch (Integra Miltex, cat #11L48). In order to preserve the original form of the wound and measure a wound-healing effect of the test substance more accurately, the wound site was bonded and sealed with the wound splint (inner diameter 7 mm, Grace Bio-Labs, Cat #1213138) as described in Galiano et al. (Wound Repair Regen July-August; 12(4):485-92, 2004; also see Li et al., J Diabetes Res 2015:512959, 2015). 20 μl of PBS (for control) or 1E4 was evenly applied to the wound area in different doses (3 μg, 6 μg, 12 μg per wound per day) using a micropipette. The wound site was then covered with TegaDerm (3M, Cat #2016-07PK) to protect the injured area. PBS or doses of 1E4 were administered daily for 14 days. Images were captured every 2 to 3 days to analyze the progression of wound closure.

Figure 1B:
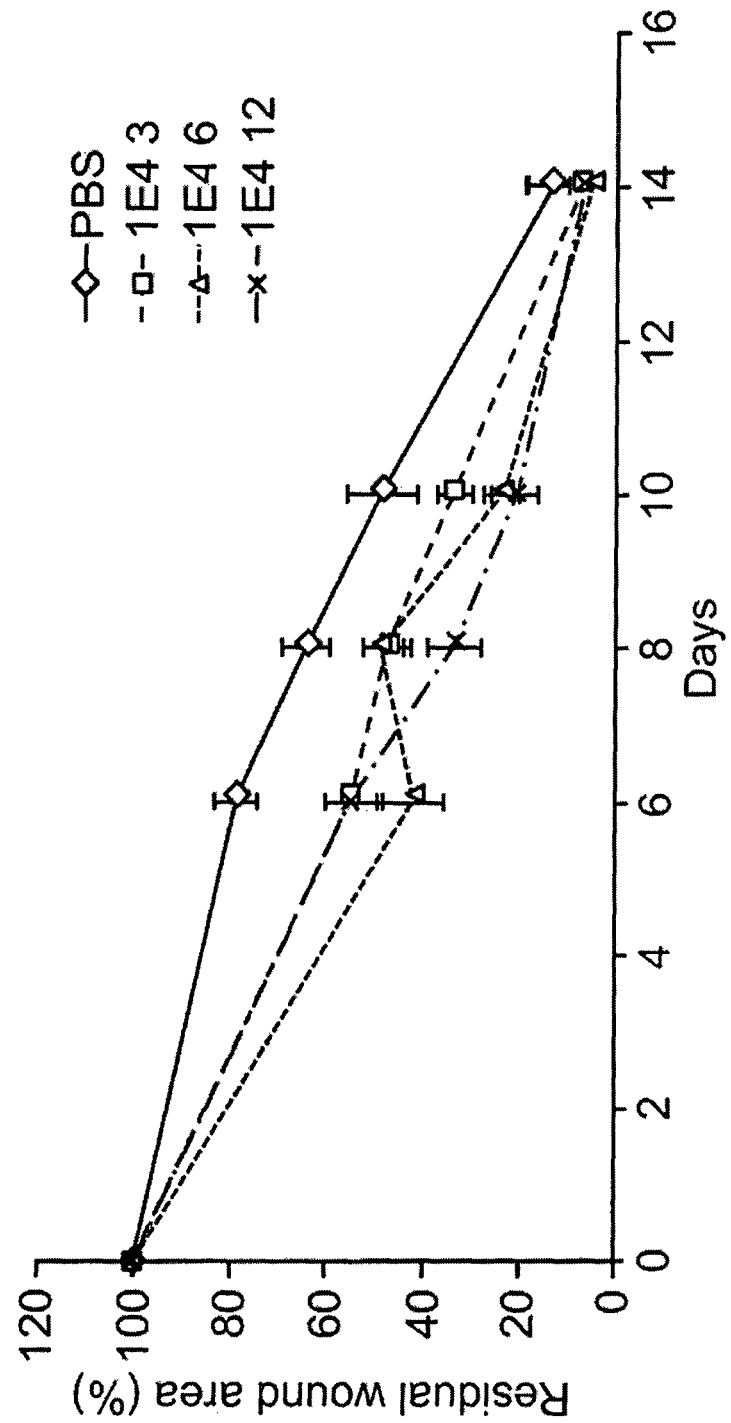

Photographs of the wound before and during treatment are provided in FIG. 1A. Corresponding measurements of wound closure are provided in the graph shown in FIG. 1B. As illustrated in FIGS. 1A and 1B, the anti c-Met antibody efficiently reduced the wound area by at least 20% more than PBS at all doses of the antibody. Accordingly, the anti c-Met antibody is effective in enhancing the wound healing process.

Example 3

Renoprotective Effects of Anti c-Met Agonist Antibodies

The anti-cancer drug adriamycin (ADR) has been reported to be nephrotoxic, and when administered to mice, levels of both blood urea nitrogen (BUN) and creatinine in blood increase due to the resulting kidney damage, as many studies have demonstrated (Rossmann et al. J Pathol. 169 (1):99-108, 1993; Wang et al.; Kidney Int. 58(4):1797-1804, 2000; Okuda et al Kidney Int 29, 502-510, 1986). Studies were done to test the ability of an agonist anti c-Met antibody to protect the kidneys from damage such as that caused by a chemotherapeutic.

Prior to administration of the 1E4 antibody, BALB/c mice (6-week-old males) underwent an acclimatization period for one week. Afterwards, PBS (control) or different doses of 1E4 (2 mg/kg, 5 mg/kg, and 10 mg/kg) were administered through tail-vein injections (Day −1). The next day (Day 0), kidney injury was induced by a single tail injection of 15 mg/kg of ADR in all animals. Two and five days after ADR injection (Days 2 and 5, respectively), PBS or corresponding doses of 1E4 were intravenously administered to the mice, respectively. On Day 7 post-ADR injection, all animals were sacrificed, and blood samples were collected to assess BUN and creatinine levels in the blood. Then the abdomen was surgically opened and a kidney was excised and fixed in 4% formaldehyde. Several slides from each kidney were prepared and stained with hematoxylin and eosin (H&E) for routine histological examination using a light microscope.

Figure 3A:
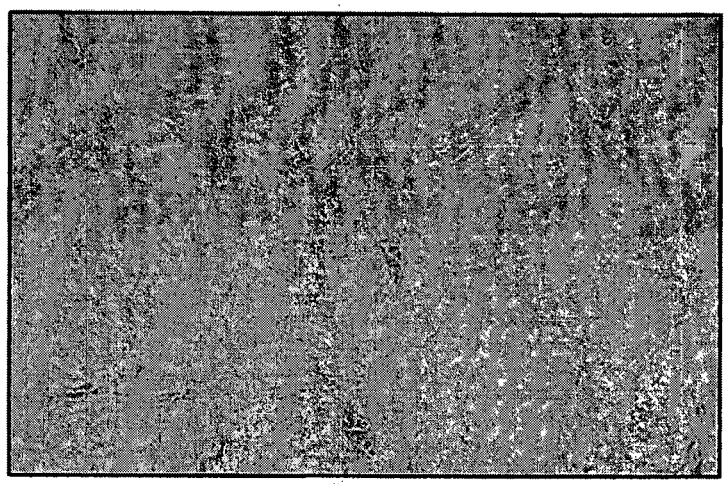
FIGS. 3A-3B show an image of a tissue section (FIG. 3A) and corresponding graph (FIG. 3B) showing the degree of kidney injury in the mice treated with an agonist anti-c-Met antibody.
Figure 3A:
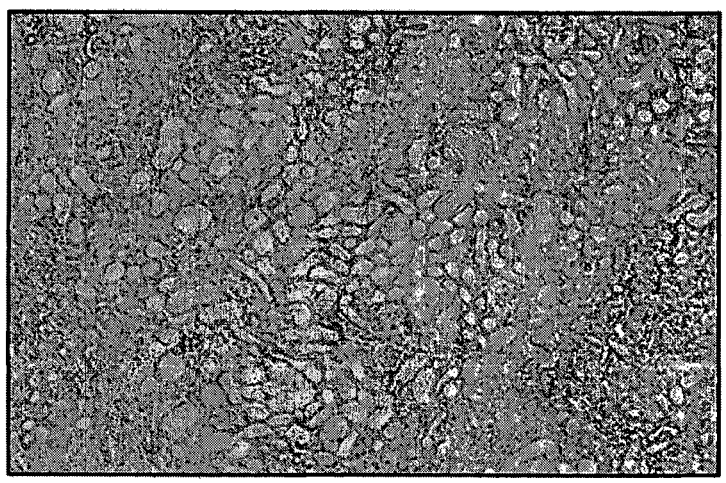
Figure 3A:
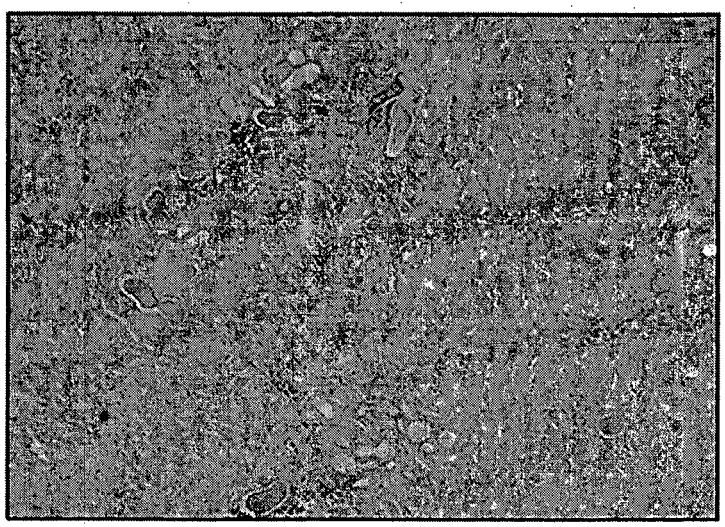
Figure 3B:
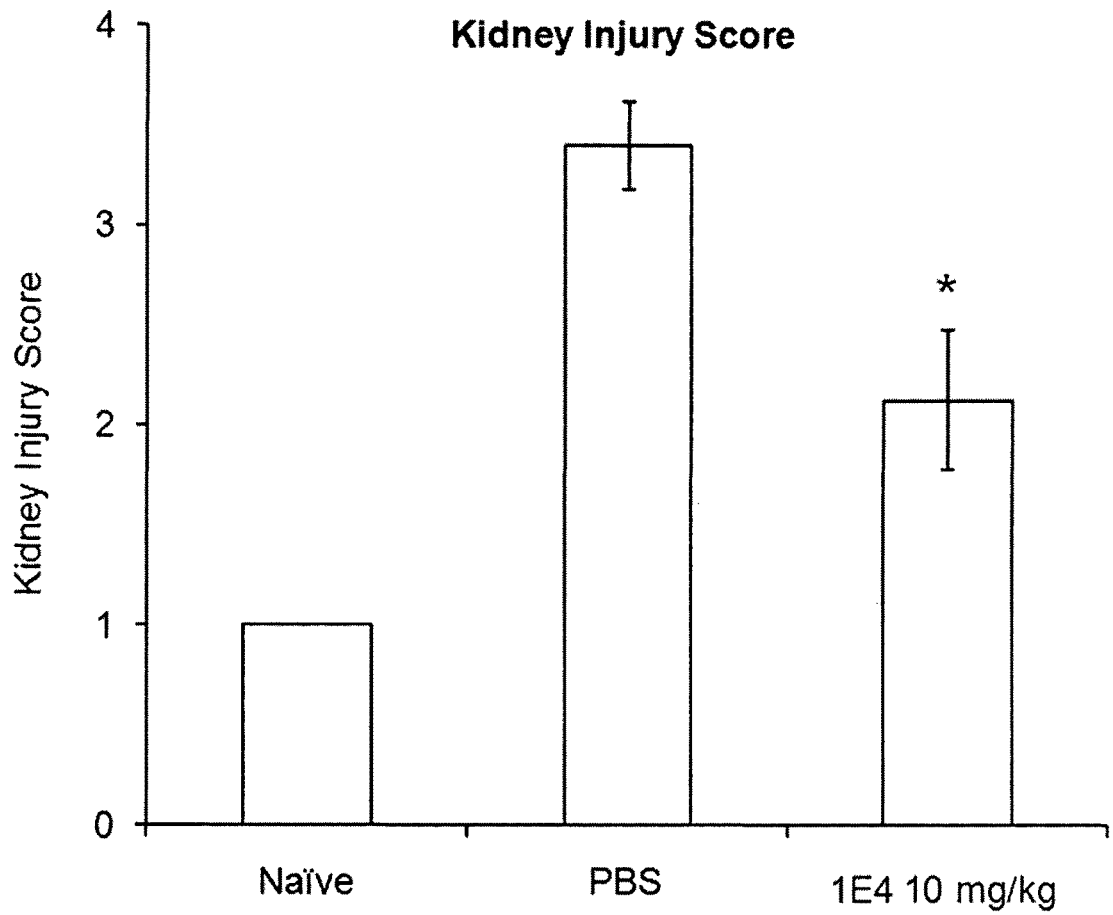

The administration of 5 mg/kg or more of the 1E4 antibody effectively reduced the increasing levels of BUN (FIG. 2A) and creatinine (FIG. 2B) in the animal model of ADR-induced kidney injury. Also, 1E4 administration at doses of 5 mg/kg and 10 mg/kg were observed to significantly improve the histologic impairment in the kidney. Images of renal H & E-stained sections are shown for tissues from naive animals, animals treated with PBS, and animals treated with 10 mg/kg 1E4 antibody (FIG. 3A). The histology analysis included assigning scores to the imaged tissues as shown in FIG. 3B. Score of 1 means the injured area is below 10% of the whole kidney tissue; score of 2 means the injured area is between 10-40% of the whole kidney tissue; score of 3 means the injured area is between 40-70% of the whole kidney tissue; score of 4 means the injured area is more than 70% of the whole kidney tissue. The asterisk indicates a significant difference at p<0.05 compared to treatment with PBS (no antibody). While an image for tissue from animals treated with 5 mg/kg 1E4 antibody is not provided here, histological analysis of these animals showed that tissue from animals treated with 5 mg/kg 1E4 antibody had a score of 2.44 with a significant difference of p<0.05, showing that both 5 mg/kg and 10 mg/kg 1E4 is effective in reducing ADR-induced kidney injury.

Example 4

Anti-Fibrotic Effects of Anti c-Met Agonist Antibodies

Unilateral ureteral obstruction (UUO) is a well-described model of renal fibrosis, a pathological hallmark of chronic kidney disease (Klahr et al. Am Physiological Soc, Vol. 283 no. 5, F861-F875, 2002; Klahr et al Nephrology Forum, Kidney Int 54:286-300, 1998). Accordingly, this animal model was used to study the effects of anti c-Met antibodies having agonist effects on fibrotic lesions in kidneys.

A day before UUO surgery, 10 mg/kg of 1E4 was injected into the tail vein of BALB/c mice. The next day, UUO surgery was performed under sterile conditions. A midline incision was made in the abdomen, and the left ureter was ligated at two points. Afterwards, the proximal segment between the two ligation points was excised. After the dissection, the abdomen was closed. Thereafter, 1E4 was administered weekly through tail vein. At 3 weeks after surgery, the left kidney was removed and fixed in 4% formaldehyde. Then, the area of the fibrotic lesion in the tissue samples was evaluated by Masson's trichrome staining and imaging of the renal sections.

Figure 4A:
FIGS. 4A-4B show a renal protective effect of an anti-c-Met agonist antibody in the rat nephropathy model induced by unilateral ureteral obstruction (UUO).
Figure 4A:
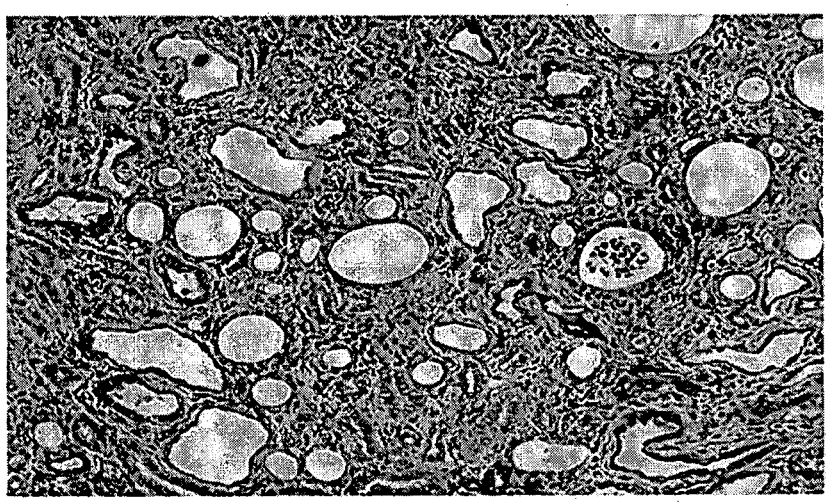
Figure 4A:
Figure 4B:
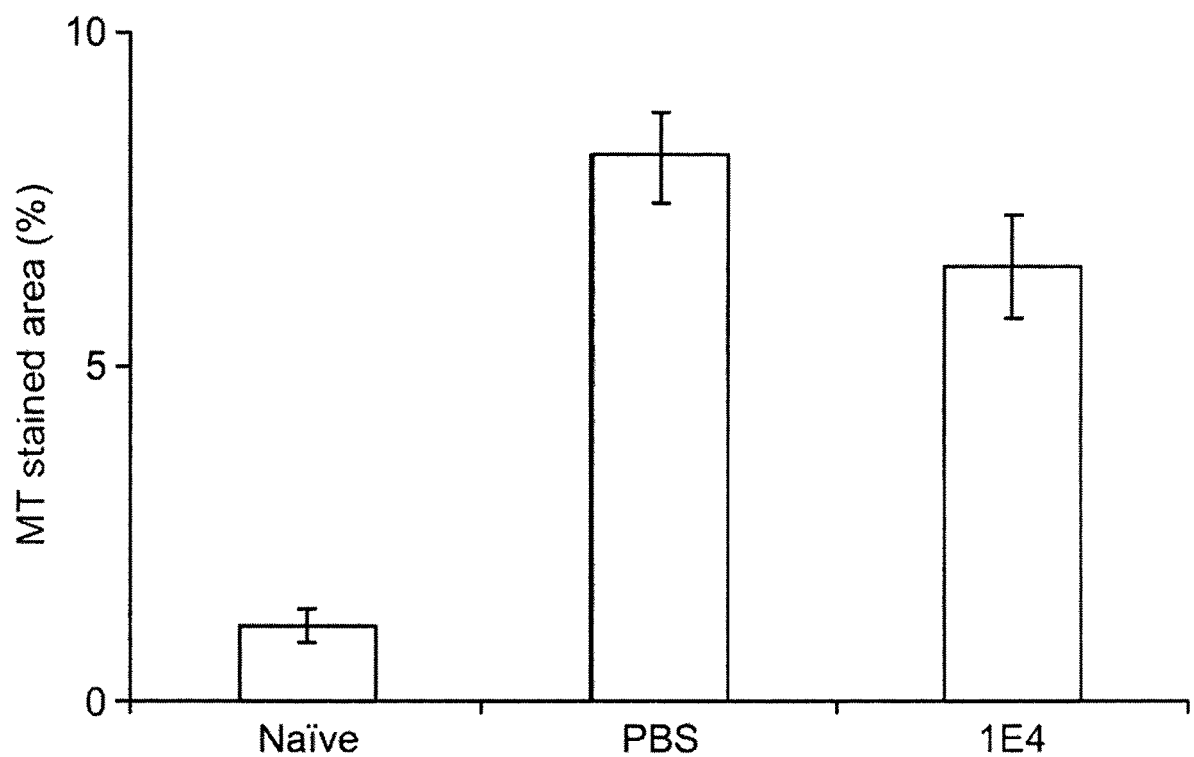

Images of the Masson's trichrome staining are provided in FIG. 4A with the corresponding quantitative analysis depicted in FIG. 4B. As shown in FIGS. 4A and 4B, administration of 1E4 is therapeutically effective in protecting the kidney from renal fibrosis.

Example 5

Treatment of Ischemic Stroke Using Anti c-Met Agonist Antibodies

The middle cerebral artery occlusion model (MCAO) is a widely utilized model in the research field of stroke. This model serves as an excellent tool to investigate underlying mechanisms of ischemic stroke and a therapeutic effect of a test substance or drug to treat the disease. (Badr et al. Am Physiological Soc, Vol. 280 no. 3:R766-R770, 2001; Zhao et al Blood, 114(15):3329-3334, 2009). Studies were performed to test the ability of the anti c-Met agonist antibody 1E4 to minimize tissue damage due to ischemic stroke or other ischemia related disorders.

The study was performed in Wistar rats (7 weeks old). A day before the induction of MCAO, 10 mg/kg of 1E4 was administered to the rats through the tail vein. The following day, the animals were anesthetized and the fur on the ventral neck region was shaved off. After the depilation, each rat was placed in a supine position. A midline incision was made above the right clavicle. The right common carotid artery (CCA) was identified and segregated from the neighboring vagus nerve. The distal branches of CCA ascending from the heart were loosely tied with a 2-0 silk. Generally, the common carotid artery bifurcates into two branches, the external carotid artery (ECA) and internal carotid artery (ICA). The ECA was tightly ligated at two points using the silk, while the ICA was loosely knotted. Subsequently, the ECA was cut between the knots. A 4-0 nylon probe with its front portion coated with silicon was inserted into the severed blood vessel for 30 minutes. After removal of the probe, the insertion site was completely sutured. 1 hour after the induction of MCAO, 10 mg/kg of 1E4 was injected intravenously using an infusion pump. Another intravenous administration of the same dose of 1E4 was performed 3 days after MCAO induction. Thereafter, 1E4 of the same dose was injected at intervals of 7 days, on Day 10, 17, and 24. The extent of infarction was quantified using an MRI (MAGNETOM ESSENZA 1.5 Tesla, SIEMENS Co., Germany) on Day 3, 7, 14, 21, and 28 after surgery.

Figure 5:
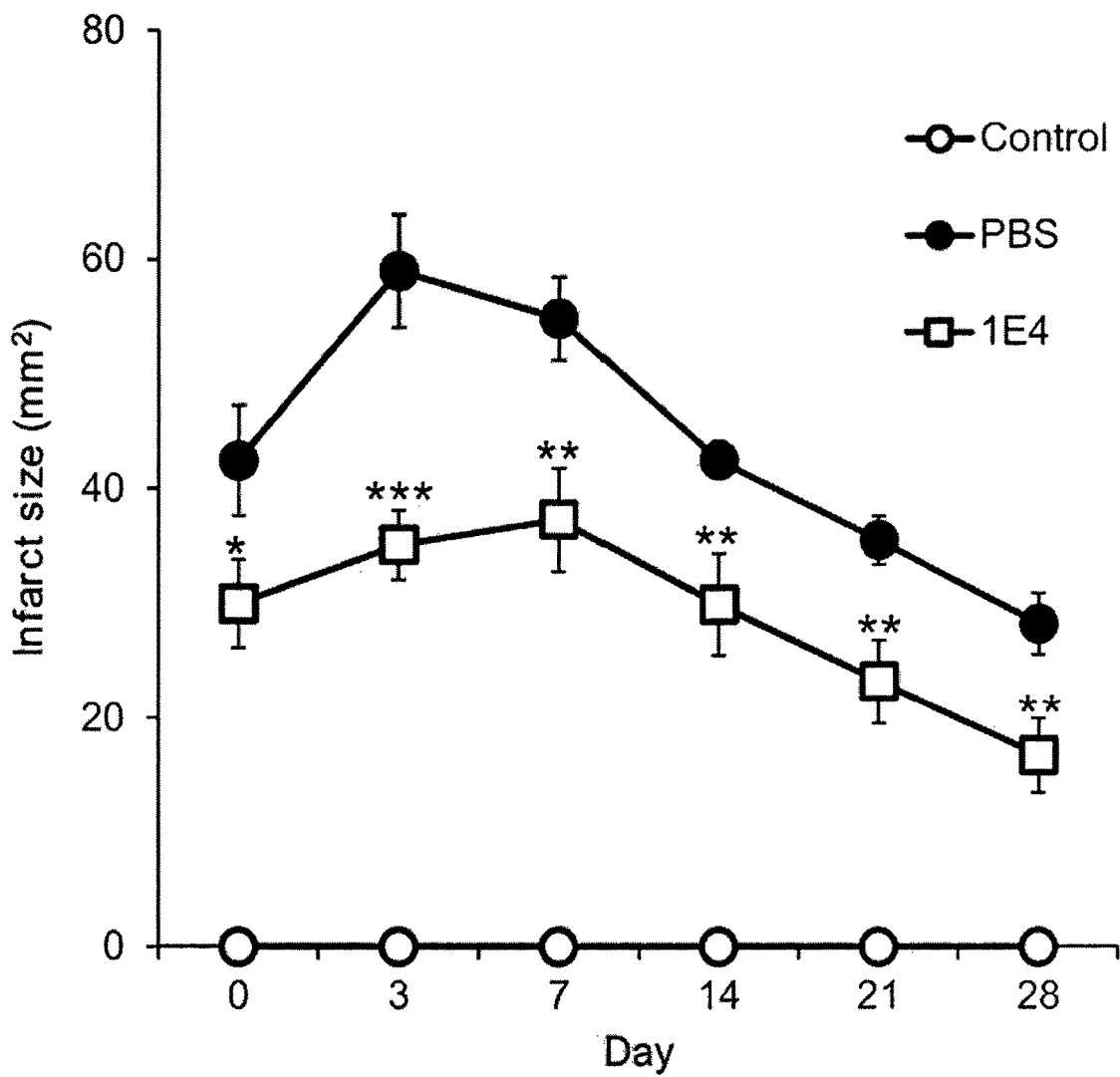
FIG. 5 shows the change in the infarct size upon treatment with an agonist anti-c-Met antibody in a rat model of ischemic stroke.

The effects as measured by MRI are shown as the measurement of infarct size in animals which were untreated or treated with PBS or 1E4 (FIG. 5). The data show that 1E4 effectively reduces brain damage caused by ischemia in the MCAO model.

Example 6

Treatment of Neovascular Retinal Diseases Using Anti c-Met Agonist Antibodies

The laser-induced choroidal neovascularization model (CNV) provides an excellent platform to examine a therapeutic effect of a drug on the pathogenic neovascularization in retina. (Marano et al. Gene Therapy, 12, 1544-1550, 2005; Zhan et al. Arch Ophthalmol, October; 127 (10): 1329-35, 2009). The CNV model was thus used to study effects of an anti c-Met agonist antibody on retinal neovascularization.

After undergoing papillary dilation with the topical application of Mydriacyl Eye Drops 1%, Chinchilla rabbits (male, 2-2.5 kg, colored) were anesthetized. A laser system (Elite, Lumenis, USA) was used to induce photocoagulation (532 nm wavelength, 150 mW power, 0.1 second duration) in the eye. Consequently, a total of 6 photocoagulation spots were created in the six o'clock position around the optic nerve. On the day of CNV induction, 50 μg of 1E4 was directly administered to the vitreous humor. On Day 0, 3, 7, 10, and 14, the animals were subjected to anesthesia after the instillation with Mydriacyl Eye Drops 1% to the right eye. The animals received 1 ml of 2% fluorescein sodium salt solution through a tail-vein injection. The fundus was visualized with an opthalmoscope (TRC-50IX, TOPCON, Japan), and images were captured within two minutes after the injection. CNV formation and efficacy of the drug were determined by measuring of the extent of diffusing fluorescence in fundus photography. Fundus images were assessed using the ImageJ software (NIH, Bethesda, Md.) to quantify the fluorescence intensity in the region with CNV. In every image, the fluorescence intensity in the region with normal blood vessels or no blood vessels was converted into the same value. The change in the final CNV value was obtained by comparing each value to that of the naive control.

Figure 6:
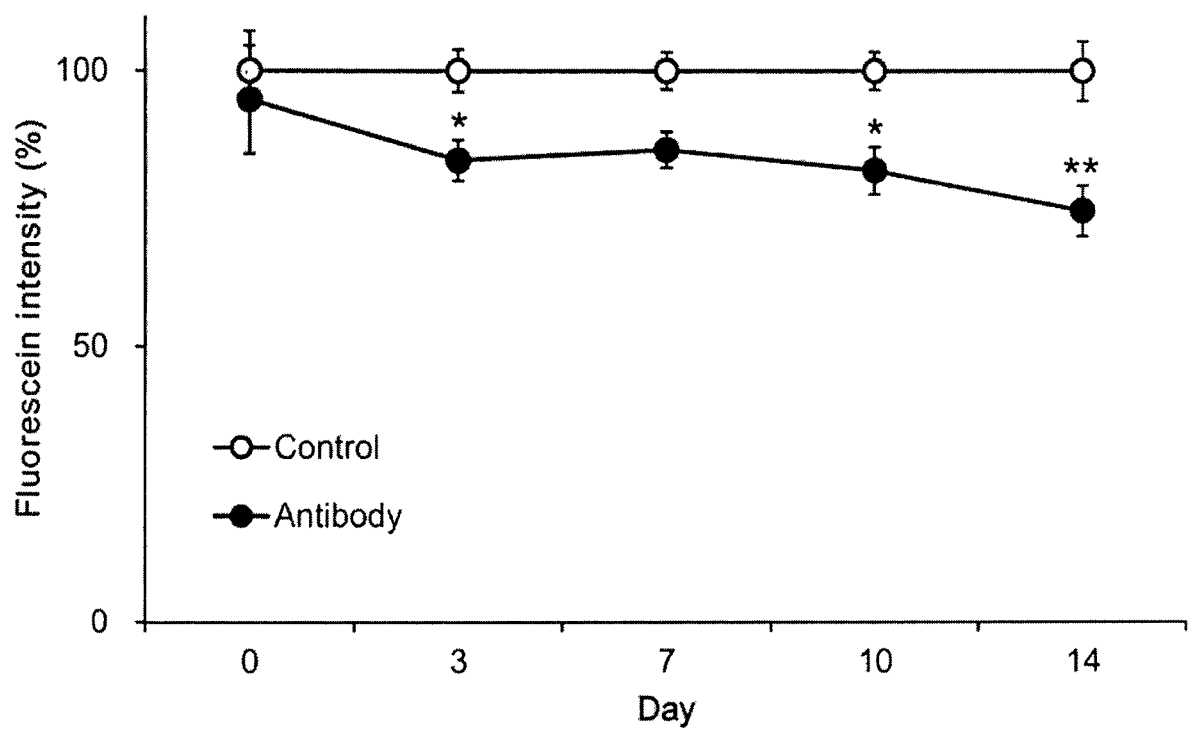
FIG. 6 is a graph showing the measurement of the fluorescence that represents choroidal neovascularization upon treatment with an agonist anti-c-Met antibody in the rabbit model of laser-induced choroidal neovascularization (CNV).

The data analysis is provided in FIG. 6 and shows that the 1E4 antibody has inhibitory effects on laser-induced CNV formation.

Example 7

Treatment of Neuronal Diseases Using Anti c-Met Agonist Antibodies

Schwann cells are known to play important roles in various aspects of the nervous system such as the nerve development, conduction (through myelination), and regeneration. Under pathological conditions, Schwann cells migrate to re-myelinate damaged nerves (Whalley Katherine, 2014, Nat Rev Neurosci.; 15(11):698-99, 2014; Jessen K R et al., 2015, Cold Spring Harb Perspect Biol.; 7(7): a020487, 2015). To examine the impact of the anti-c-Met antibody 1E4 on Schwann cell migration, Rat Schwann cells (iSC) were cultured in complete medium containing Dulbecco's modified eagle's medium supplemented with 10% fetal bovine serum (FBS), glutamine, penicillin/streptomycin, and HEPES. For the migration assay, the Transwell (Corning, 3422) inserts were coated with 0.1% gelatin (Sigma, G1393) for 45 min in cell incubator (37° C. and 5% $CO_2$). Rat Schwann cells were seeded onto the upper compartments of the Transwell system in 100 ul of complete medium after digestion by 0.25% trypsin-EDTA. The bottom chambers were filled with 600 µl of full growth medium with 2% FBS. The Transwell system was then incubated for 50 min at 37° C. and 5% $CO_2$ for the cells to settle down. Subsequently, the growth medium at the bottom chambers was supplemented with 50 ng/ml recombinant human HGF (R&D systems, 294-HGF-025/CF) or different concentrations of 1E4 as follows: 900 ng/ml, 450 ng/ml, 90 ng/ml, and 18 ng/ml. Cell migration across the Transwell filter was allowed to proceed for 4 hr. Cells on the Transwell inserts were fixed with 4% formaldehyde overnight at 4° C. After fixation, cells were stained with 0.2% crystal violet with the non-migrated cells on the top of the filters removed with a cotton swab. Five images were taken using Olympus microscope to count the number of migrated cells and determine an average for the filter.

As shown in FIGS. 7A and 7B, 1E4 at all indicated concentrations significantly increased migration of Schwann cells as compared to cells treated with PBS (no 1E4).

Example 8

Treatment of Amyotrophic Lateral Sclerosis Using Anti c-Met Agonist Antibodies B6SJL-Tg (SOD1-G93A) mice expressing human mutant SOD1 are transgenic animals which are an accepted animal model for evaluating therapeutic efficacy of a drug for treating ALS: (Ji-Seon Seo et al, Exp Neurobiol., December; 24(4): 341-350, 2015; Gurney M E et al., Science., 264: 1772-1775, 1994) and other neuromuscular disorders. Accordingly, studies were done to test the effects of 1E4 antibody administration on the onset of ALS symptoms in the model animals. Based on behavioral assessment with the Rotarod, the mice were divided into groups. After classification, 1E4 was intra-thecally administered at 20 µg per mouse. One week later, each mouse received 10 mg/kg of 1E4 through intra-peritoneal injection. This alternate treatment of intra-thecal and intra-peritoneal 1E4 injection was continued for the following 2 weeks. After that 2 week period, 10 mg/kg of 1E4 was only peritoneally administered to the mice every week until the end of the experiment. Motor function was measured with the Rotarod and grip strength tests once per week and survival was monitored three times per week.

After the fourth week, when the onset of ALS-related symptoms are expected to appear, the mice started to show an improved motor function in response to 1E4 administration (FIGS. 8A and 8B) as compared to treatment with PBS alone. Also, 1E4 treatment increased the survival of the mice (FIG. 8D).

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A method for treating a disease selected from the group consisting of ischemic disorder, stroke, kidney injury or disease, retinal neovascularization disorder, amyotrophic lateral sclerosis, and wound healing, the method comprising administering to a subject in need thereof a therapeutically effective amount of a polypeptide or a pharmaceutical composition comprising the polypeptide, wherein the polypeptide comprises an immunoglobulin heavy chain variable domain which comprises a CDR1 of SEQ ID NO:5, a CDR2 of SEQ ID NO:6, a CDR3 of SEQ ID NO:7, and a light chain variable domain which comprises a CDR1 of SEQ ID NO:8, a CDR2 of SEQ ID NO:9, and a CDR3 of SEQ ID NO:10.

2. The method according to claim 1, wherein the ischemic disorder is selected from the group consisting of ischemia of brain tissue, heart tissue, kidney tissue, or intestinal tissue.

3. The method according to claim 1, wherein the stroke is an embolic stroke or a thrombotic stroke.

4. The method according to claim 1, wherein the kidney injury or disease is a fibrotic condition.

5. The method according to claim 1, wherein the kidney injury or disease is selected from the group consisting of renal fibrosis, chronic kidney fibrosis, chronic nephropathy associated with diabetes, lupus, scleroderma of the kidney, glomerular nephritis, focal segmental glomerular sclerosis, IgA nephropathyrenal fibrosis associated with human chronic kidney disease (CD), chronic progressive nephropathy (CPN), tubulointerstitial fibrosis, ureteral obstruction, chronic uremia, chronic interstitial nephritis, radiation nephropathy, glomerulosclerosis, progressive glomerulonephrosis (PGN), endothelial/thrombotic microangiopathy injury, HIV-associated nephropathy, and a fibrosis associated with exposure to a toxin, an irritant, or a chemotherapeutic agent.

6. The method according to claim 1, wherein the retinal neovascularization disorder is caused by a member selected from the group consisting of macular degeneration, histoplasmosis, pathological myopia, angioid streaks, anterior ischemic optic neuropathy, bacterial endocarditis, Best's disease, birdshot retinochoroidopathy, choroidal hemangioma, choroidal nevi, choroidal nonperfusion, choroidal osteomas, choroidal rupture, chorioderemia, chronic retinal detachment, coloboma of the retina, Drusen, endogenous *Candida endophthalmitis*, extrapapillary hamartomas of the retinal pigmented epithelium, fundus flavimaculatus, idiopathic, macular hole, malignant melanoma, membranoproliferative glomerulonephritis (type II), metallic intraocular foreign body, morning glory disc syndrome, multiple evanescent white-dot syndrome (MEWDS), neovascularization at or a serrata, operating microscope burn, optic nerve head pits, photocoagulation, punctuate inner choroidopathy, rubella, sarcoidosis, serpiginous or geographic choroiditis, subretinal fluid drainage, tilted disc syndrome, Taxoplasma retinochoroiditis, tuberculosis, Vogt-Koyanagi-Harada syndrome, diabetic retinopathy, non-diabetic retinopathy, branch vein occlusion, central retinal vein occlusion, retinopathy in premature infants, rubeosis iridis, neovascular glaucoma, periofoveal telangiectasis, sickle cell retinopathy, Eales disease, retinal vasculitis, Von Hippel Linau disease, radiation retinopathy, retinal cryoinjury, retinitis pigmentosa, retinochoroidal coloboma, corneal neovascularization due to herpes simplex keratitis, corneal ulcers, keratoplasty, pterigyia, and trauma.

7. The method according to claim 1, wherein the retinal neovascularization disorder is choroidal neovascularization.

8. The method according to claim 1, wherein the wound is a mechanical, chemical, bacterial, or thermal wound.

9. The method according to claim 1, wherein the wound is selected from the group consisting of an incision, a laceration, an abrasion, a puncture wound, a penetration wound, and a gunshot wound.

10. The method according to claim 1, wherein the wound is a skin wound.

11. The method according to claim 1, wherein the heavy chain variable domain comprises SEQ ID NO:1 and the light chain variable domain comprises SEQ ID NO:2.

12. The method according to claim 1 wherein the polypeptide is an antibody or fragment thereof.

13. The method according to claim 12, wherein the antibody or fragment thereof is a chimeric antibody, a humanized antibody, or a human antibody.

14. The method according to claim 1, wherein the polypeptide comprises a scFv.

15. The method according to claim 14, wherein the heavy chain variable domain comprises SEQ ID NO:1 and the light chain variable domain comprises SEQ ID NO:2.

16. The method according to claim 14, wherein the scFv comprises SEQ ID NO:3.

17. The method according to claim 1, wherein the administering is intravenous, intravitreal, intrathecal, parenteral, subcutaneous, topical, transdermal or by infusion.

18. The method according to claim 1, wherein the subject is not suffering from a cancer.

* * * * *

SEQUENCE LISTING

<160> NUMBER OF SEQ ID NOS: 15

<210> SEQ ID NO 1
<211> LENGTH: 126
<212> TYPE: PRT
<213> ORGANISM: Artificial Sequence
<220> FEATURE:
<223> OTHER INFORMATION: Synthetic Construct

<400> SEQUENCE: 1

```
Gln Val Gln Leu Val Gln Ser Gly Ala Glu Val Lys Lys Pro Gly Glu
1               5                   10                  15

Ser Leu Arg Ile Ser Cys Gln Gly Ser Gly Tyr Ser Phe Pro Thr His
            20                  25                  30

Trp Ile Thr Trp Val Arg Gln Met Pro Gly Lys Gly Leu Glu Trp Met
        35                  40                  45

Gly Thr Ile Asp Pro Thr Asp Ser Tyr Asn Phe Tyr Gly Pro Ser Phe
    50                  55                  60

Gln Gly His Val Thr Ile Ser Ala Asp Ser Ser Ser Thr Ala Tyr
65                  70                  75                  80
```

```
Leu Gln Trp Ser Ser Leu Lys Ala Ser Asp Thr Ala Met Tyr Tyr Cys
                85                  90                  95

Ala Arg Asp Gly Asn Tyr Tyr Asp Ser Arg Gly Tyr Tyr Asp Thr
            100                 105                 110

Phe Asp Met Trp Gly Gln Gly Thr Leu Val Thr Val Ser Ser
        115                 120                 125

<210> SEQ ID NO 2
<211> LENGTH: 115
<212> TYPE: PRT
<213> ORGANISM: Artificial Sequence
<220> FEATURE:
<223> OTHER INFORMATION: Synthetic Construct

<400> SEQUENCE: 2

Asp Ile Gln Met Thr Gln Ser Pro Ser Phe Leu Ser Ala Ser Val Gly
1               5                   10                  15

Asp Arg Val Thr Ile Thr Cys Arg Ala Ser Gln Gly Ile Ser Thr Tyr
            20                  25                  30

Leu Ala Trp Tyr Gln Gln Lys Pro Gly Thr Ala Pro Lys Leu Leu Ile
        35                  40                  45

Tyr Ser Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ser Ala Thr Tyr Tyr Cys Gln Gln Ala Asp Ser Phe Pro Leu
                85                  90                  95

Thr Phe Gly Gly Gly Thr Lys Val Glu Ile Lys Arg Gly Gly Ala Ser
            100                 105                 110

Leu Val Glu
        115

<210> SEQ ID NO 3
<211> LENGTH: 264
<212> TYPE: PRT
<213> ORGANISM: Artificial Sequence
<220> FEATURE:
<223> OTHER INFORMATION: Synthetic Construct

<400> SEQUENCE: 3

Gln Val Gln Leu Val Gln Ser Gly Ala Glu Val Lys Lys Pro Gly Glu
1               5                   10                  15

Ser Leu Arg Ile Ser Cys Gln Gly Ser Gly Tyr Ser Phe Pro Thr His
            20                  25                  30

Trp Ile Thr Trp Val Arg Gln Met Pro Gly Lys Gly Leu Glu Trp Met
        35                  40                  45

Gly Thr Ile Asp Pro Thr Asp Ser Tyr Asn Phe Tyr Gly Pro Ser Phe
    50                  55                  60

Gln Gly His Val Thr Ile Ser Ala Asp Ser Ser Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Gly Asn Tyr Tyr Asp Ser Arg Gly Tyr Tyr Asp Thr
            100                 105                 110

Phe Asp Met Trp Gly Gln Gly Thr Leu Val Thr Val Ser Ser Gly Leu
        115                 120                 125

Gly Gly Leu Gly Gly Gly Gly Ser Gly Gly Gly Gly Ser Gly Gly Ser
    130                 135                 140
```

```
Ser Gly Val Gly Ser Asp Ile Gln Met Thr Gln Ser Pro Ser Phe Leu
145                 150                 155                 160

Ser Ala Ser Val Gly Asp Arg Val Thr Ile Thr Cys Arg Ala Ser Gln
            165                 170                 175

Gly Ile Ser Thr Tyr Leu Ala Trp Tyr Gln Gln Lys Pro Gly Thr Ala
        180                 185                 190

Pro Lys Leu Leu Ile Tyr Ser Ala Ser Thr Leu Glu Ser Gly Val Pro
    195                 200                 205

Ser Arg Phe Ser Gly Ser Gly Ser Gly Thr Asp Phe Thr Leu Thr Ile
210                 215                 220

Ser Ser Leu Gln Pro Glu Asp Ser Ala Thr Tyr Tyr Cys Gln Gln Ala
225                 230                 235                 240

Asp Ser Phe Pro Leu Thr Phe Gly Gly Gly Thr Lys Val Glu Ile Lys
            245                 250                 255

Arg Gly Gly Ala Ser Leu Val Glu
            260

<210> SEQ ID NO 4
<211> LENGTH: 23
<212> TYPE: PRT
<213> ORGANISM: Artificial Sequence
<220> FEATURE:
<223> OTHER INFORMATION: Synthetic Construct

<400> SEQUENCE: 4

Gly Leu Gly Gly Leu Gly Gly Gly Ser Gly Gly Gly Ser Gly
1               5                   10                  15

Gly Ser Ser Gly Val Gly Ser
            20

<210> SEQ ID NO 5
<211> LENGTH: 5
<212> TYPE: PRT
<213> ORGANISM: Artificial Sequence
<220> FEATURE:
<223> OTHER INFORMATION: Synthetic Construct

<400> SEQUENCE: 5

Thr His Trp Ile Thr
1               5

<210> SEQ ID NO 6
<211> LENGTH: 17
<212> TYPE: PRT
<213> ORGANISM: Artificial Sequence
<220> FEATURE:
<223> OTHER INFORMATION: Synthetic Construct

<400> SEQUENCE: 6

Thr Ile Asp Pro Thr Asp Ser Tyr Asn Phe Tyr Gly Pro Ser Phe Gln
1               5                   10                  15

Gly

<210> SEQ ID NO 7
<211> LENGTH: 17
<212> TYPE: PRT
<213> ORGANISM: Artificial Sequence
<220> FEATURE:
<223> OTHER INFORMATION: Synthetic Construct

<400> SEQUENCE: 7
```

Asp Gly Asn Tyr Tyr Asp Ser Arg Gly Tyr Tyr Asp Thr Phe Asp
1               5                   10                  15

Met

<210> SEQ ID NO 8
<211> LENGTH: 11
<212> TYPE: PRT
<213> ORGANISM: Artificial Sequence
<220> FEATURE:
<223> OTHER INFORMATION: Synthetic Construct

<400> SEQUENCE: 8

Arg Ala Ser Gln Gly Ile Ser Thr Tyr Leu Ala
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Synthetic Construct

<400> SEQUENCE: 9

Ser Ala Ser Thr Leu Glu Ser
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic Construct

<400> SEQUENCE: 10

Gln Gln Ala Asp Ser Phe Pro Leu Thr
1               5

<210> SEQ ID NO 11
<211> LENGTH: 378
<212> TYPE: DNA
<213> ORGANISM: Artificial Sequence
<220> FEATURE:
<223> OTHER INFORMATION: Synthetic Construct

<400> SEQUENCE: 11
caggtgcagc tggtgcagtc tggagcagag gtgaaaaagc ccggggagtc tctgaggatc      60
tcctgtcagg gttctggata cagttttccc acccactgga tcacctgggt gcgccagatg     120
cccgggaaag gcctggagtg gatgggaacg attgatccta ctgactctta caatttctat     180
ggaccgtcgt tccaaggcca cgtcaccatc tcagccgaca gctccagcag caccgcctac     240
ctgcagtgga gcagcctgaa ggcctcggac accgccatgt attactgtgc gagagatggc     300
aactactatg atagtcgcgg ttattactac gatactttg atatgtgggg ccaagggaca     360
ctggtcaccg tctcctca                                                   378

<210> SEQ ID NO 12
<211> LENGTH: 348
<212> TYPE: DNA
<213> ORGANISM: Artificial Sequence
<220> FEATURE:
<223> OTHER INFORMATION: Synthetic Construct

<400> SEQUENCE: 12
tccgacatcc agatgaccca gtctccatcc ttcctctctg catctgtcgg agacagagtc      60

-continued

```
accatcactt gccgggccag tcagggcatc agtacttatt agcctggta tcaacaaaaa    120 ccagggacag cccctaaact cctgatctat tctgcatcca ctttggaaag tggggtccca    180
tcgcgattca gcggaagtgg atccgggaca gatttcactc tcaccatcag cagcctgcag    240
cctgaagatt ctgcaactta ctattgtcaa caggctgaca gtttcccgct cactttcggc    300
ggagggacca aggtggagat caaacgtgga ggagccagcc tcgtggaa                 348
```

<210> SEQ ID NO 13
<211> LENGTH: 1390
<212> TYPE: PRT
<213> ORGANISM: homo sapiens

<400> SEQUENCE: 13

```
Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
        195                 200                 205

His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
        275                 280                 285

His Ser Tyr Met Glu Met Pro Leu Glu Cys Ile Leu Thr Glu Lys Arg
    290                 295                 300

Lys Lys Arg Ser Thr Lys Lys Glu Val Phe Asn Ile Leu Gln Ala Ala
305                 310                 315                 320
```

-continued

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
            340                 345                 350

Ser Ala Glu Pro Met Asp Arg Ser Ala Met Cys Ala Phe Pro Ile Lys
        355                 360                 365

Tyr Val Asn Asp Phe Phe Asn Lys Ile Val Asn Lys Asn Asn Val Arg
    370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
            420                 425                 430

Gln Phe Ser Glu Val Leu Leu Thr Ser Ile Ser Thr Phe Ile Lys Gly
        435                 440                 445

Asp Leu Thr Ile Ala Asn Leu Gly Thr Ser Glu Gly Arg Phe Met Gln
    450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
            500                 505                 510

Ile Pro Leu Asn Gly Leu Gly Cys Arg His Phe Gln Ser Cys Ser Gln
        515                 520                 525

Cys Leu Ser Ala Pro Pro Phe Val Gln Cys Gly Trp Cys His Asp Lys
    530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
            580                 585                 590

Asn Asn Lys Phe Asp Leu Lys Lys Thr Arg Val Leu Leu Gly Asn Glu
        595                 600                 605

Ser Cys Thr Leu Thr Leu Ser Glu Ser Thr Met Asn Thr Leu Lys Cys
    610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                645                 650                 655

Pro Val Ile Thr Ser Ile Ser Pro Lys Tyr Gly Pro Met Ala Gly Gly
            660                 665                 670

Thr Leu Leu Thr Leu Thr Gly Asn Tyr Leu Asn Ser Gly Asn Ser Arg
        675                 680                 685

His Ile Ser Ile Gly Gly Lys Thr Cys Thr Leu Lys Ser Val Ser Asn
    690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser

```
                    740                 745                 750
Phe Ile Ser Gly Gly Ser Thr Ile Thr Gly Val Gly Lys Asn Leu Asn
                755                 760                 765

Ser Val Ser Val Pro Arg Met Val Ile Asn Val His Glu Ala Gly Arg
                770                 775             780

Asn Phe Thr Val Ala Cys Gln His Arg Ser Asn Ser Glu Ile Ile Cys
785                 790                 795                 800

Cys Thr Thr Pro Ser Leu Gln Gln Leu Asn Leu Gln Leu Pro Leu Lys
                    805                 810                 815

Thr Lys Ala Phe Phe Met Leu Asp Gly Ile Leu Ser Lys Tyr Phe Asp
                820                 825                 830

Leu Ile Tyr Val His Asn Pro Val Phe Lys Pro Phe Glu Lys Pro Val
                835                 840                 845

Met Ile Ser Met Gly Asn Glu Asn Val Leu Glu Ile Lys Gly Asn Asp
                850                 855                 860

Ile Asp Pro Glu Ala Val Lys Gly Glu Val Leu Lys Val Gly Asn Lys
865                 870                 875                 880

Ser Cys Glu Asn Ile His Leu His Ser Glu Ala Val Leu Cys Thr Val
                    885                 890                 895

Pro Asn Asp Leu Leu Lys Leu Asn Ser Glu Leu Asn Ile Glu Trp Lys
                900                 905                 910

Gln Ala Ile Ser Ser Thr Val Leu Gly Lys Val Ile Val Gln Pro Asp
                915                 920                 925

Gln Asn Phe Thr Gly Leu Ile Ala Gly Val Val Ser Ile Ser Thr Ala
                930                 935                 940

Leu Leu Leu Leu Leu Gly Phe Phe Leu Trp Leu Lys Lys Arg Lys Gln
945                 950                 955                 960

Ile Lys Asp Leu Gly Ser Glu Leu Val Arg Tyr Asp Ala Arg Val His
                965                 970                 975

Thr Pro His Leu Asp Arg Leu Val Ser Ala Arg Ser Val Ser Pro Thr
                980                 985                 990

Thr Glu Met Val Ser Asn Glu Ser  Val Asp Tyr Arg Ala  Thr Phe Pro
                995                 1000                1005

Glu Asp Gln Phe Pro Asn Ser  Ser Gln Asn Gly Ser  Cys Arg Gln
    1010                1015                1020

Val Gln Tyr Pro Leu Thr Asp Met Ser Pro Ile Leu  Thr Ser Gly
    1025                1030                1035

Asp Ser  Asp Ile Ser Ser Pro  Leu Leu Gln Asn Thr  Val His Ile
    1040                1045                1050

Asp Leu  Ser Ala Leu Asn Pro  Glu Leu Val Gln Ala  Val Gln His
    1055                1060                1065

Val Val  Ile Gly Pro Ser Ser  Leu Ile Val His Phe  Asn Glu Val
    1070                1075                1080

Ile Gly  Arg Gly His Phe Gly  Cys Val Tyr His Gly  Thr Leu Leu
    1085                1090                1095

Asp Asn  Asp Gly Lys Lys Ile  His Cys Ala Val Lys  Ser Leu Asn
    1100                1105                1110

Arg Ile  Thr Asp Ile Gly Glu  Val Ser Gln Phe Leu  Thr Glu Gly
    1115                1120                1125

Ile Ile  Met Lys Asp Phe Ser  His Pro Asn Val Leu  Ser Leu Leu
    1130                1135                1140

Gly Ile  Cys Leu Arg Ser Glu  Gly Ser Pro Leu Val  Val Leu Pro
    1145                1150                1155
```

Tyr Met Lys His Gly Asp Leu Arg Asn Phe Ile Arg Asn Glu Thr
    1160            1165                1170

His Asn Pro Thr Val Lys Asp Leu Ile Gly Phe Gly Leu Gln Val
    1175            1180                1185

Ala Lys Gly Met Lys Tyr Leu Ala Ser Lys Lys Phe Val His Arg
    1190            1195                1200

Asp Leu Ala Ala Arg Asn Cys Met Leu Asp Glu Lys Phe Thr Val
    1205            1210                1215

Lys Val Ala Asp Phe Gly Leu Ala Arg Asp Met Tyr Asp Lys Glu
    1220            1225                1230

Tyr Tyr Ser Val His Asn Lys Thr Gly Ala Lys Leu Pro Val Lys
    1235            1240                1245

Trp Met Ala Leu Glu Ser Leu Gln Thr Gln Lys Phe Thr Thr Lys
    1250            1255                1260

Ser Asp Val Trp Ser Phe Gly Val Leu Leu Trp Glu Leu Met Thr
    1265            1270                1275

Arg Gly Ala Pro Pro Tyr Pro Asp Val Asn Thr Phe Asp Ile Thr
    1280            1285                1290

Val Tyr Leu Leu Gln Gly Arg Arg Leu Leu Gln Pro Glu Tyr Cys
    1295            1300                1305

Pro Asp Pro Leu Tyr Glu Val Met Leu Lys Cys Trp His Pro Lys
    1310            1315                1320

Ala Glu Met Arg Pro Ser Phe Ser Glu Leu Val Ser Arg Ile Ser
    1325            1330                1335

Ala Ile Phe Ser Thr Phe Ile Gly Glu His Tyr Val His Val Asn
    1340            1345                1350

Ala Thr Tyr Val Asn Val Lys Cys Val Ala Pro Tyr Pro Ser Leu
    1355            1360                1365

Leu Ser Ser Glu Asp Asn Ala Asp Asp Glu Val Asp Thr Arg Pro
    1370            1375                1380

Ala Ser Phe Trp Glu Thr Ser
    1385            1390

<210> SEQ ID NO 14
<211> LENGTH: 1408
<212> TYPE: PRT
<213> ORGANISM: homo sapiens

<400> SEQUENCE: 14

Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
                20                  25                  30

Ser Glu Met Asn Val Asn Met Lys Tyr Gln Leu Pro Asn Phe Thr Ala
            35                  40                  45

Glu Thr Pro Ile Gln Asn Val Ile Leu His Glu His His Ile Phe Leu
        50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp

```
            115                 120                 125
Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
                195                 200                 205

His Pro Leu His Ser Ile Ser Val Arg Arg Leu Lys Glu Thr Lys Asp
210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
                260                 265                 270

Thr Phe His Thr Arg Ile Ile Arg Phe Cys Ser Ile Asn Ser Gly Leu
            275                 280                 285

His Ser Tyr Met Glu Met Pro Leu Glu Cys Ile Leu Thr Glu Lys Arg
    290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
                340                 345                 350

Ser Ala Glu Pro Met Asp Arg Ser Ala Met Cys Ala Phe Pro Ile Lys
            355                 360                 365

Tyr Val Asn Asp Phe Phe Asn Lys Ile Val Asn Lys Asn Asn Val Arg
    370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
                420                 425                 430

Gln Phe Ser Glu Val Leu Leu Thr Ser Ile Ser Thr Phe Ile Lys Gly
            435                 440                 445

Asp Leu Thr Ile Ala Asn Leu Gly Thr Ser Glu Gly Arg Phe Met Gln
    450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
                500                 505                 510

Ile Pro Leu Asn Gly Leu Gly Cys Arg His Phe Gln Ser Cys Ser Gln
            515                 520                 525

Cys Leu Ser Ala Pro Pro Phe Val Gln Cys Gly Trp Cys His Asp Lys
530                 535                 540
```

```
Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
            565                 570                 575

Gly Gly Thr Arg Leu Thr Ile Cys Gly Trp Asp Phe Gly Phe Arg Arg
            580                 585                 590

Asn Asn Lys Phe Asp Leu Lys Lys Thr Arg Val Leu Leu Gly Asn Glu
            595                 600                 605

Ser Cys Thr Leu Thr Leu Ser Glu Ser Thr Met Asn Thr Leu Lys Cys
            610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
            645                 650                 655

Pro Val Ile Thr Ser Ile Ser Pro Lys Tyr Gly Pro Met Ala Gly Gly
            660                 665                 670

Thr Leu Leu Thr Leu Thr Gly Asn Tyr Leu Asn Ser Gly Asn Ser Arg
            675                 680                 685

His Ile Ser Ile Gly Gly Lys Thr Cys Thr Leu Lys Ser Val Ser Asn
690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
            725                 730                 735

Ser Tyr Arg Glu Asp Pro Ile Val Tyr Glu Ile His Pro Thr Lys Ser
            740                 745                 750

Phe Ile Ser Thr Trp Trp Lys Glu Pro Leu Asn Ile Val Ser Phe Leu
            755                 760                 765

Phe Cys Phe Ala Ser Gly Gly Ser Thr Ile Thr Gly Val Gly Lys Asn
            770                 775                 780

Leu Asn Ser Val Ser Val Pro Arg Met Val Ile Asn Val His Glu Ala
785                 790                 795                 800

Gly Arg Asn Phe Thr Val Ala Cys Gln His Arg Ser Asn Ser Glu Ile
            805                 810                 815

Ile Cys Cys Thr Thr Pro Ser Leu Gln Gln Leu Asn Leu Gln Leu Pro
            820                 825                 830

Leu Lys Thr Lys Ala Phe Phe Met Leu Asp Gly Ile Leu Ser Lys Tyr
            835                 840                 845

Phe Asp Leu Ile Tyr Val His Asn Pro Val Phe Lys Pro Phe Glu Lys
850                 855                 860

Pro Val Met Ile Ser Met Gly Asn Glu Asn Val Leu Glu Ile Lys Gly
865                 870                 875                 880

Asn Asp Ile Asp Pro Glu Ala Val Lys Gly Glu Val Leu Lys Val Gly
            885                 890                 895

Asn Lys Ser Cys Glu Asn Ile His Leu His Ser Glu Ala Val Leu Cys
            900                 905                 910

Thr Val Pro Asn Asp Leu Leu Lys Leu Asn Ser Glu Leu Asn Ile Glu
            915                 920                 925

Trp Lys Gln Ala Ile Ser Ser Thr Val Leu Gly Lys Val Ile Val Gln
            930                 935                 940

Pro Asp Gln Asn Phe Thr Gly Leu Ile Ala Gly Val Val Ser Ile Ser
945                 950                 955                 960
```

Thr Ala Leu Leu Leu Leu Gly Phe Phe Leu Trp Leu Lys Lys Arg
            965                 970                 975

Lys Gln Ile Lys Asp Leu Gly Ser Glu Leu Val Arg Tyr Asp Ala Arg
            980                 985                 990

Val His Thr Pro His Leu Asp Arg  Leu Val Ser Ala Arg  Ser Val Ser
        995             1000                 1005

Pro Thr  Thr Glu Met Val Ser  Asn Glu Ser Val Asp  Tyr Arg Ala
    1010             1015             1020

Thr Phe  Pro Glu Asp Gln Phe  Pro Asn Ser Ser Gln  Asn Gly Ser
    1025             1030             1035

Cys Arg  Gln Val Gln Tyr Pro  Leu Thr Asp Met Ser  Pro Ile Leu
    1040             1045             1050

Thr Ser  Gly Asp Ser Asp Ile  Ser Ser Pro Leu Leu  Gln Asn Thr
    1055             1060             1065

Val His  Ile Asp Leu Ser Ala  Leu Asn Pro Glu Leu  Val Gln Ala
    1070             1075             1080

Val Gln  His Val Val Ile Gly  Pro Ser Ser Leu Ile  Val His Phe
    1085             1090             1095

Asn Glu  Val Ile Gly Arg Gly  His Phe Gly Cys Val  Tyr His Gly
    1100             1105             1110

Thr Leu  Leu Asp Asn Asp Gly  Lys Lys Ile His Cys  Ala Val Lys
    1115             1120             1125

Ser Leu  Asn Arg Ile Thr Asp  Ile Gly Glu Val Ser  Gln Phe Leu
    1130             1135             1140

Thr Glu  Gly Ile Ile Met Lys  Asp Phe Ser His Pro  Asn Val Leu
    1145             1150             1155

Ser Leu  Leu Gly Ile Cys Leu  Arg Ser Glu Gly Ser  Pro Leu Val
    1160             1165             1170

Val Leu  Pro Tyr Met Lys His  Gly Asp Leu Arg Asn  Phe Ile Arg
    1175             1180             1185

Asn Glu  Thr His Asn Pro Thr  Val Lys Asp Leu Ile  Gly Phe Gly
    1190             1195             1200

Leu Gln  Val Ala Lys Gly Met  Lys Tyr Leu Ala Ser  Lys Lys Phe
    1205             1210             1215

Val His  Arg Asp Leu Ala Ala  Arg Asn Cys Met Leu  Asp Glu Lys
    1220             1225             1230

Phe Thr  Val Lys Val Ala Asp  Phe Gly Leu Ala Arg  Asp Met Tyr
    1235             1240             1245

Asp Lys  Glu Tyr Tyr Ser Val  His Asn Lys Thr Gly  Ala Lys Leu
    1250             1255             1260

Pro Val  Lys Trp Met Ala Leu  Glu Ser Leu Gln Thr  Gln Lys Phe
    1265             1270             1275

Thr Thr  Lys Ser Asp Val Trp  Ser Phe Gly Val Leu  Leu Trp Glu
    1280             1285             1290

Leu Met  Thr Arg Gly Ala Pro  Pro Tyr Pro Asp Val  Asn Thr Phe
    1295             1300             1305

Asp Ile  Thr Val Tyr Leu Leu  Gln Gly Arg Arg Leu  Leu Gln Pro
    1310             1315             1320

Glu Tyr  Cys Pro Asp Pro Leu  Tyr Glu Val Met Leu  Lys Cys Trp
    1325             1330             1335

His Pro  Lys Ala Glu Met Arg  Pro Ser Phe Ser Glu  Leu Val Ser
    1340             1345             1350

Arg Ile  Ser Ala Ile Phe Ser  Thr Phe Ile Gly Glu  His Tyr Val

```
                    1355                1360                1365

His Val Asn Ala Thr Tyr Val Asn Val Lys Cys Val Ala Pro Tyr
        1370                1375                1380

Pro Ser Leu Leu Ser Ser Glu Asp Asn Ala Asp Asp Glu Val Asp
    1385                1390                1395

Thr Arg Pro Ala Ser Phe Trp Glu Thr Ser
    1400                1405

<210> SEQ ID NO 15
<211> LENGTH: 1379
<212> TYPE: PRT
<213> ORGANISM: mus musculus

<400> SEQUENCE: 15

Met Lys Ala Pro Thr Val Leu Ala Pro Gly Ile Leu Val Leu Leu
1               5                   10                  15

Ser Leu Val Gln Arg Ser His Gly Glu Cys Lys Glu Ala Leu Val Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Val Leu His Gly His His Ile Tyr Leu
    50                  55                  60

Gly Ala Thr Asn Tyr Ile Tyr Val Leu Asn Asp Lys Asp Leu Gln Lys
65                  70                  75                  80

Val Ser Glu Phe Lys Thr Gly Pro Val Leu Glu His Pro Asp Cys Leu
                85                  90                  95

Pro Cys Arg Asp Cys Ser Ser Lys Ala Asn Ser Ser Gly Gly Val Trp
            100                 105                 110

Lys Asp Asn Ile Asn Met Ala Leu Leu Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Leu Pro Pro Asp Asn Ser Ala Asp Ile Gln Ser Glu Val His Cys
145                 150                 155                 160

Met Phe Ser Pro Glu Glu Glu Ser Gly Gln Cys Pro Asp Cys Val Val
                165                 170                 175

Ser Ala Leu Gly Ala Lys Val Leu Leu Ser Glu Lys Asp Arg Phe Ile
            180                 185                 190

Asn Phe Phe Val Gly Asn Thr Ile Asn Ser Ser Tyr Pro Pro Gly Tyr
        195                 200                 205

Ser Leu His Ser Ile Ser Val Arg Arg Leu Lys Glu Thr Gln Asp Gly
    210                 215                 220

Phe Lys Phe Leu Thr Asp Gln Ser Tyr Ile Asp Val Leu Pro Glu Phe
225                 230                 235                 240

Gln Asp Ser Tyr Pro Ile Lys Tyr Ile His Ala Phe Glu Ser Asn His
                245                 250                 255

Phe Ile Tyr Phe Leu Thr Val Gln Lys Glu Thr Leu Asp Ala Gln Thr
            260                 265                 270

Phe His Thr Arg Ile Ile Arg Phe Cys Ser Val Asp Ser Gly Leu His
        275                 280                 285

Ser Tyr Met Glu Met Pro Leu Glu Cys Ile Leu Thr Glu Lys Arg Arg
    290                 295                 300

Lys Arg Ser Thr Arg Glu Glu Val Phe Asn Ile Leu Gln Ala Ala Tyr
305                 310                 315                 320
```

```
Val Ser Lys Pro Gly Ala Asn Leu Ala Lys Gln Ile Gly Ala Ser Pro
            325                 330                 335

Ser Asp Asp Ile Leu Phe Gly Val Phe Ala Gln Ser Lys Pro Asp Ser
        340                 345                 350

Ala Glu Pro Val Asn Arg Ser Ala Val Cys Ala Phe Pro Ile Lys Tyr
            355                 360                 365

Val Asn Asp Phe Phe Asn Lys Ile Val Asn Lys Asn Val Arg Cys
370                 375                 380

Leu Gln His Phe Tyr Gly Pro Asn His Glu His Cys Phe Asn Arg Thr
385                 390                 395                 400

Leu Leu Arg Asn Ser Ser Gly Cys Glu Ala Arg Ser Asp Glu Tyr Arg
                405                 410                 415

Thr Glu Phe Thr Thr Ala Leu Gln Arg Val Asp Leu Phe Met Gly Arg
            420                 425                 430

Leu Asn Gln Val Leu Leu Thr Ser Ile Ser Thr Phe Ile Lys Gly Asp
                435                 440                 445

Leu Thr Ile Ala Asn Leu Gly Thr Ser Glu Gly Arg Phe Met Gln Val
    450                 455                 460

Val Leu Ser Arg Thr Ala His Leu Thr Pro His Val Asn Phe Leu Leu
465                 470                 475                 480

Asp Ser His Pro Val Ser Pro Glu Val Ile Val Glu His Pro Ser Asn
                485                 490                 495

Gln Asn Gly Tyr Thr Leu Val Val Thr Gly Lys Lys Ile Thr Lys Ile
            500                 505                 510

Pro Leu Asn Gly Leu Gly Cys Gly His Phe Gln Ser Cys Ser Gln Cys
        515                 520                 525

Leu Ser Ala Pro Tyr Phe Ile Gln Cys Gly Trp Cys His Asn Gln Cys
    530                 535                 540

Val Arg Phe Asp Glu Cys Pro Ser Gly Thr Trp Thr Gln Glu Ile Cys
545                 550                 555                 560

Leu Pro Ala Val Tyr Lys Val Phe Pro Thr Ser Ala Pro Leu Glu Gly
                565                 570                 575

Gly Thr Val Leu Thr Ile Cys Gly Trp Asp Phe Gly Phe Arg Lys Asn
            580                 585                 590

Asn Lys Phe Asp Leu Arg Lys Thr Lys Val Leu Leu Gly Asn Glu Ser
        595                 600                 605

Cys Thr Leu Thr Leu Ser Glu Ser Thr Thr Asn Thr Leu Lys Cys Thr
    610                 615                 620

Val Gly Pro Ala Met Ser Glu His Phe Asn Val Ser Val Ile Ile Ser
625                 630                 635                 640

Asn Ser Arg Glu Thr Thr Gln Tyr Ser Ala Phe Ser Tyr Val Asp Pro
                645                 650                 655

Val Ile Thr Ser Ile Ser Pro Arg Tyr Gly Pro Gln Ala Gly Gly Thr
            660                 665                 670

Leu Leu Thr Leu Thr Gly Lys Tyr Leu Asn Ser Gly Asn Ser Arg His
        675                 680                 685

Ile Ser Ile Gly Gly Lys Thr Cys Thr Leu Lys Ser Val Ser Asp Ser
    690                 695                 700

Ile Leu Glu Cys Tyr Thr Pro Ala Gln Thr Thr Ser Asp Glu Phe Pro
705                 710                 715                 720

Val Lys Leu Lys Ile Asp Leu Ala Asn Arg Glu Thr Ser Ser Phe Ser
                725                 730                 735

Tyr Arg Glu Asp Pro Val Val Tyr Glu Ile His Pro Thr Lys Ser Phe
```

```
                  740             745             750
Ile Ser Gly Gly Ser Thr Ile Thr Gly Ile Gly Lys Thr Leu Asn Ser
            755             760             765

Val Ser Leu Pro Lys Leu Val Ile Asp Val His Glu Val Gly Val Asn
            770             775             780

Tyr Thr Val Ala Cys Gln His Arg Ser Asn Ser Glu Ile Ile Cys Cys
785             790             795             800

Thr Thr Pro Ser Leu Lys Gln Leu Gly Leu Gln Leu Pro Leu Lys Thr
                805             810             815

Lys Ala Phe Phe Leu Leu Asp Gly Ile Leu Ser Lys His Phe Asp Leu
                820             825             830

Thr Tyr Val His Asn Pro Val Phe Glu Pro Phe Glu Lys Pro Val Met
            835             840             845

Ile Ser Ile Gly Asn Glu Asn Val Val Glu Ile Lys Gly Asn Asn Ile
        850             855             860

Asp Pro Glu Ala Val Lys Gly Glu Val Leu Lys Val Gly Asn Gln Ser
865             870             875             880

Cys Glu Ser Leu His Trp His Ser Gly Ala Val Leu Cys Thr Val Pro
                885             890             895

Ser Asp Leu Leu Lys Leu Asn Ser Glu Leu Asn Ile Glu Trp Lys Gln
                900             905             910

Ala Val Ser Ser Thr Val Leu Gly Lys Val Ile Val Gln Pro Asp Gln
            915             920             925

Asn Phe Ala Gly Leu Ile Ile Gly Ala Val Ser Ile Ser Val Val Val
        930             935             940

Leu Leu Leu Ser Gly Leu Phe Leu Trp Met Arg Lys Arg Lys His Lys
945             950             955             960

Asp Leu Gly Ser Glu Leu Val Arg Tyr Asp Ala Arg Val His Thr Pro
                965             970             975

His Leu Asp Arg Leu Val Ser Ala Arg Ser Val Ser Pro Thr Thr Glu
                980             985             990

Met Val Ser Asn Glu Ser Val Asp  Tyr Arg Ala Thr Phe  Pro Glu Asp
            995             1000            1005

Gln Phe  Pro Asn Ser Ser Gln  Asn Gly Ala Cys Arg  Gln Val Gln
    1010            1015            1020

Tyr Pro  Leu Thr Asp Leu Ser  Pro Ile Leu Thr Ser  Gly Asp Ser
    1025            1030            1035

Asp Ile  Ser Ser Pro Leu Leu  Gln Asn Thr Val His  Ile Asp Leu
    1040            1045            1050

Ser Ala  Leu Asn Pro Glu Leu  Val Gln Ala Val Gln  His Val Val
    1055            1060            1065

Ile Gly  Pro Ser Ser Leu Ile  Val His Phe Asn Glu  Val Ile Gly
    1070            1075            1080

Arg Gly  His Phe Gly Cys Val  Tyr His Gly Thr Leu  Leu Asp Asn
    1085            1090            1095

Asp Gly  Lys Lys Ile His Cys  Ala Val Lys Ser Leu  Asn Arg Ile
    1100            1105            1110

Thr Asp  Ile Glu Glu Val Ser  Gln Phe Leu Thr Glu  Gly Ile Ile
    1115            1120            1125

Met Lys  Asp Phe Ser His Pro  Asn Val Leu Ser Leu  Leu Gly Ile
    1130            1135            1140

Cys Leu  Arg Ser Glu Gly Ser  Pro Leu Val Val Leu  Pro Tyr Met
    1145            1150            1155
```

```
            Lys His Gly Asp Leu Arg Asn Phe Ile Arg Asn Glu Thr His Asn
                1160            1165            1170

Pro Thr Val Lys Asp Leu Ile Gly Phe Gly Leu Gln Val Ala Lys
                1175            1180            1185

Gly Met Lys Tyr Leu Ala Ser Lys Lys Phe Val His Arg Asp Leu
                1190            1195            1200

Ala Ala Arg Asn Cys Met Leu Asp Glu Lys Phe Thr Val Lys Val
                1205            1210            1215

Ala Asp Phe Gly Leu Ala Arg Asp Met Tyr Asp Lys Glu Tyr Tyr
                1220            1225            1230

Ser Val His Asn Lys Thr Gly Ala Lys Leu Pro Val Lys Trp Met
                1235            1240            1245

Ala Leu Glu Ser Leu Gln Thr Gln Lys Phe Thr Thr Lys Ser Asp
                1250            1255            1260

Val Trp Ser Phe Gly Val Leu Leu Trp Glu Leu Met Thr Arg Gly
                1265            1270            1275

Ala Pro Pro Tyr Pro Asp Val Asn Thr Phe Asp Ile Thr Ile Tyr
                1280            1285            1290

Leu Leu Gln Gly Arg Arg Leu Leu Gln Pro Glu Tyr Cys Pro Asp
                1295            1300            1305

Ala Leu Tyr Glu Val Met Leu Lys Cys Trp His Pro Lys Ala Glu
                1310            1315            1320

Met Arg Pro Ser Phe Ser Glu Leu Val Ser Arg Ile Ser Ser Ile
                1325            1330            1335

Phe Ser Thr Phe Ile Gly Glu His Tyr Val His Val Asn Ala Thr
                1340            1345            1350

Tyr Val Asn Val Lys Cys Val Ala Pro Tyr Pro Ser Leu Leu Pro
                1355            1360            1365

Ser Gln Asp Asn Ile Asp Gly Glu Gly Asn Thr
                1370            1375
```